(12) United States Patent
Westacott et al.

(10) Patent No.: US 11,851,965 B2
(45) Date of Patent: Dec. 26, 2023

(54) CORE SAMPLING AND ANALYSIS USING A SEALED PRESSURIZED VESSEL

(71) Applicant: Halliburton Energy Services, Inc., Houston, TX (US)

(72) Inventors: Donald Clifford Westacott, Spring, TX (US); Christopher Michael Jones, Katy, TX (US); Anthony Herman van Zuilekom, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 381 days.

(21) Appl. No.: 17/077,653

(22) Filed: Oct. 22, 2020

(65) Prior Publication Data

US 2021/0123344 A1 Apr. 29, 2021

Related U.S. Application Data

(60) Provisional application No. 62/932,982, filed on Nov. 8, 2019, provisional application No. 62/925,620, filed on Oct. 24, 2019.

(51) Int. Cl.
  *E21B 25/10* (2006.01)
  *E21B 49/08* (2006.01)
  (Continued)

(52) U.S. Cl.
  CPC .............. *E21B 25/10* (2013.01); *E21B 47/07* (2020.05); *E21B 49/06* (2013.01);
  (Continued)

(58) Field of Classification Search
  CPC .......... E21B 25/10; E21B 47/07; E21B 49/06; E21B 49/0875; E21B 10/02; E21B 25/00;
  (Continued)

(56) References Cited

U.S. PATENT DOCUMENTS 3,295,896 A 1/1967 Ingvar et al.
3,305,191 A 2/1967 Fritz
(Continued)

FOREIGN PATENT DOCUMENTS

CN 104458914 A 3/2015
JP 6095217 B2 3/2017
(Continued)

OTHER PUBLICATIONS

PCT Application No. PCT/US2020/056861, International Preliminary Report on Patentability, dated May 5, 2022, 8 pages.
(Continued)

*Primary Examiner* — Marrit Eyassu
(74) *Attorney, Agent, or Firm* — DELIZIO, PEACOCK, LEWIN & GUERRA

(57) ABSTRACT

Disclosed are methods, systems, and devices for measuring and otherwise processing core samples. In some embodiments, a method includes containing a core sample in a containment vessel including dynamically adjusting pressure within the containment vessel to maintain a phase of fluid within the core sample. Pressure is reduced within the containment vessel. During pressure or following reduction, one or more properties of the fluid in the core sample are measured.

22 Claims, 20 Drawing Sheets

(51) Int. Cl.

| | | |
|---|---|---|
| *E21B 49/06* | (2006.01) | |
| *G01N 1/22* | (2006.01) | |
| *G01N 23/046* | (2018.01) | |
| *G01N 24/08* | (2006.01) | |
| *G01N 33/00* | (2006.01) | |
| *G01N 33/24* | (2006.01) | |
| *G01V 9/00* | (2006.01) | |
| *E21B 47/07* | (2012.01) | |
| *G01N 1/08* | (2006.01) | |
| *E21B 10/02* | (2006.01) | |

(52) U.S. Cl.
CPC ........... *E21B 49/0875* (2020.05); *G01N 1/08* (2013.01); *G01N 1/2202* (2013.01); *G01N 23/046* (2013.01); *G01N 24/081* (2013.01); *G01N 33/0016* (2013.01); *G01N 33/24* (2013.01); *G01V 9/00* (2013.01); *E21B 10/02* (2013.01); *G01N 2223/616* (2013.01)

(58) Field of Classification Search
CPC ........ E21B 49/08; G01N 1/08; G01N 1/2202; G01N 23/046; G01N 24/081; G01N 33/0016; G01N 33/24; G01N 2223/616; G01N 3/12; G01N 7/00; G01V 9/00; G01R 33/30
USPC ........................................................ 73/19.01
See application file for complete search history.

(56) References Cited

U.S. PATENT DOCUMENTS

| | | | |
|---|---|---|---|
| 4,256,192 A | | 3/1981 | Aumann |
| 4,258,803 A | | 3/1981 | Thompson et al. |
| 4,317,490 A | | 3/1982 | Milberger et al. |
| 4,515,503 A | | 5/1985 | Snowdon |
| 4,710,948 A | | 12/1987 | Withjack et al. |
| 4,916,945 A | | 4/1990 | Weisbrod et al. |
| 5,253,720 A | | 10/1993 | Radford et al. |
| 5,869,750 A | * | 2/1999 | Onan ................. G01N 33/383 73/64.41 |
| 5,934,374 A | * | 8/1999 | Hrametz ................. E21B 49/10 166/264 |
| 6,106,202 A | | 8/2000 | Nolan |
| 6,216,804 B1 | * | 4/2001 | Aumann ................. E21B 25/08 175/246 |
| 6,230,825 B1 | | 5/2001 | Aumann et al. |
| 6,305,482 B1 | | 10/2001 | Aumann et al. |
| 6,378,631 B1 | | 4/2002 | Aumann et al. |
| 8,920,029 B2 | | 12/2014 | Maucec et al. |
| 9,650,891 B2 | | 5/2017 | Reid et al. |
| 9,874,063 B2 | | 1/2018 | Arian et al. |
| 9,951,574 B2 | | 4/2018 | Westacott et al. |
| 10,221,684 B2 | | 3/2019 | Westacott et al. |
| 10,301,936 B2 | | 5/2019 | Westacott et al. |
| 10,317,351 B2 | | 6/2019 | Chong et al. |
| 10,550,655 B2 | | 4/2020 | Jones et al. |
| 10,761,157 B2 | | 9/2020 | Chen et al. |
| 2002/0033281 A1 | | 3/2002 | Aumann et al. |
| 2008/0115577 A1 | * | 5/2008 | Headrick ............... G01N 9/002 73/32 A |
| 2010/0126266 A1 | | 5/2010 | Coenen |
| 2011/0094295 A1 | * | 4/2011 | Meadows ................ G01N 3/08 73/38 |
| 2011/0247879 A1 | * | 10/2011 | Johnston ................. E21B 25/00 175/58 |
| 2014/0262532 A1 | | 9/2014 | Mizuguchi et al. |
| 2015/0021097 A1 | | 1/2015 | Wesemeier et al. |
| 2016/0194955 A1 | | 7/2016 | Delmar et al. |
| 2017/0089158 A1 | * | 3/2017 | Gupta .................... G01N 33/24 |
| 2018/0045008 A1 | | 2/2018 | Gupta et al. |
| 2018/0051559 A1 | | 2/2018 | Westacott et al. |
| 2018/0148988 A1 | * | 5/2018 | Dusterhoft .............. E21B 25/10 |
| 2018/0163535 A1 | | 6/2018 | Quintero et al. |
| 2018/0245415 A1 | * | 8/2018 | Jones ...................... E21B 47/07 |
| 2018/0259465 A1 | | 9/2018 | Chong et al. |
| 2018/0259467 A1 | | 9/2018 | Buono et al. |
| 2018/0292477 A1 | | 10/2018 | Chen et al. |
| 2018/0298709 A1 | | 10/2018 | Gupta et al. |
| 2020/0225177 A1 | | 7/2020 | Sungkorn et al. |
| 2021/0032947 A1 | * | 2/2021 | Montoya ................. G01R 33/12 |
| 2021/0032987 A1 | * | 2/2021 | Seltzer ................... G01R 33/12 |
| 2021/0123313 A1 | | 4/2021 | Westacott et al. |
| 2021/0389294 A1 | | 12/2021 | Krueger et al. |

FOREIGN PATENT DOCUMENTS

| | | |
|---|---|---|
| KR | 20140001408 A | 1/2014 |
| WO | 2021081202 A1 | 4/2021 |
| WO | 2021081202 A9 | 4/2021 |
| WO | 2021081216 | 4/2021 |

OTHER PUBLICATIONS

PCT Application No. PCT/US2020/056880, International Preliminary Report on Patentability, dated May 5, 2022, 7 pages.

U.S. Appl. No. 17/077,791, Restriction Requirement, dated Jul. 25, 2022, 7 pages.

U.S. Appl. No. 17/077,791, Non-Final Office Action, dated Sep. 13, 2022, 9 pages.

Pinkett, et al., "Innovative Sidewall Pressure Coring Technology Improves Reservoir Insight in Multiple Applications", Society of Petrophysicists and Well-Log Analysts, SPWLA 57th Annual Logging Symposium, Jun. 25-29, 2016, Reykjavik, Iceland, 15 pages.

PCT Application No. PCT/US2020/056861, International Search Report, dated Feb. 10, 2021, 3 pages.

PCT Application No. PCT/US2020/056861, Written Opinion, dated Feb. 10, 2021, 6 pages.

PCT Application No. PCT/US2020/056880, International Search Report, dated Feb. 10, 2021, 4 pages.

PCT Application No. PCT/US2020/056880, Written Opinion, dated Feb. 10, 2021, 5 pages.

* cited by examiner

CORE SAMPLING AND ANALYSIS USING A SEALED PRESSURIZED VESSEL

RELATED APPLICATIONS

This application claims the benefit of priority to U.S. Provisional Application Ser. No. 62/925,620, filed Oct. 24, 2019, and the benefit of priority to U.S. Provisional Application Ser. No. 62/932,982, filed Nov. 8, 2019, both of which are hereby incorporated by reference in their entireties.

BACKGROUND

The disclosure generally relates to the field of formation test operations, and more particularly to downhole core sampling and analysis.

In the process of conducting coring operations within an oil or gas wellbore, a coring tool is run downhole by wireline conveyance and multiple core samples are cut from the wellbore. The core samples are placed within a pressure vessel in the wellbore. The pressure vessel is then sealed downhole with a plug that retains the recovered core samples and fluids during recovery of the pressure vessel to the surface. The core samples are subsequently shipped offsite for detailed laboratory analysis. The sealed pressure vessel containing the core samples cannot be opened outside of the laboratory without risking adverse effects on the quality and integrity of the core samples. Further, the use of certain implements to determine the volume of the core samples within the pressure vessel such as, for example, X-ray machines and/or CT scan machines, is often precluded by the design and construction of the pressure vessel itself. As a result, the volume of the core samples within the pressure vessel recovered from the wellbore is often unknown before the pressure vessel is opened in the laboratory.

BRIEF DESCRIPTION OF THE DRAWINGS

Embodiments of the disclosure may be better understood by referencing the accompanying drawings.

DETAILED DESCRIPTION

The description that follows includes example systems, methods, techniques, and program flows that embody aspects of the disclosure. However, it is understood that this disclosure may be practiced without these specific details. In other instances, well-known instruction instances, protocols, structures and techniques have not been shown in detail in order not to obfuscate the description.

Various embodiments include a coring tool for extraction of a core from a subsurface formation. Various embodiments include different improvements for such a coring tool. As further detailed below, example embodiments can include pressure-temperature compensation for a coring tool using a nitrogen accumulator, bubble point determination of the extracted core sample, a coring tool that includes a Nuclear Magnetic Resonance (NMR) and Computed Tomography (CT) Transparent pressure vessel, pressure core transfer, automated gas desorption, Archimedes bulk volume modification, and constant volumetric rate depletion.

Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented in which the coring tool is made suitable for testing, retrieval and sampling along sections of the formation. Embodiments may be implemented with various samplers that, for example, may be conveyed through flow passage in tubular string or conveyance, such as using a wireline, slickline, coiled tubing, downhole robot (tractor), or the like. The system described herein may be suited for use with the Hostile Rotary Sidewall Coring Tool (HRSCT-B) available from Halliburton Energy Services of Houston, Tex., for example. The method described herein may be used in one or more of wireline, measurement-while-drilling (MWD) and logging-while-drilling (LWD) operations. One or more illustrative embodiments disclosed herein are presented below. Not all features of an actual implementation are described or shown in this application for the sake of clarity.

Figure 1A:
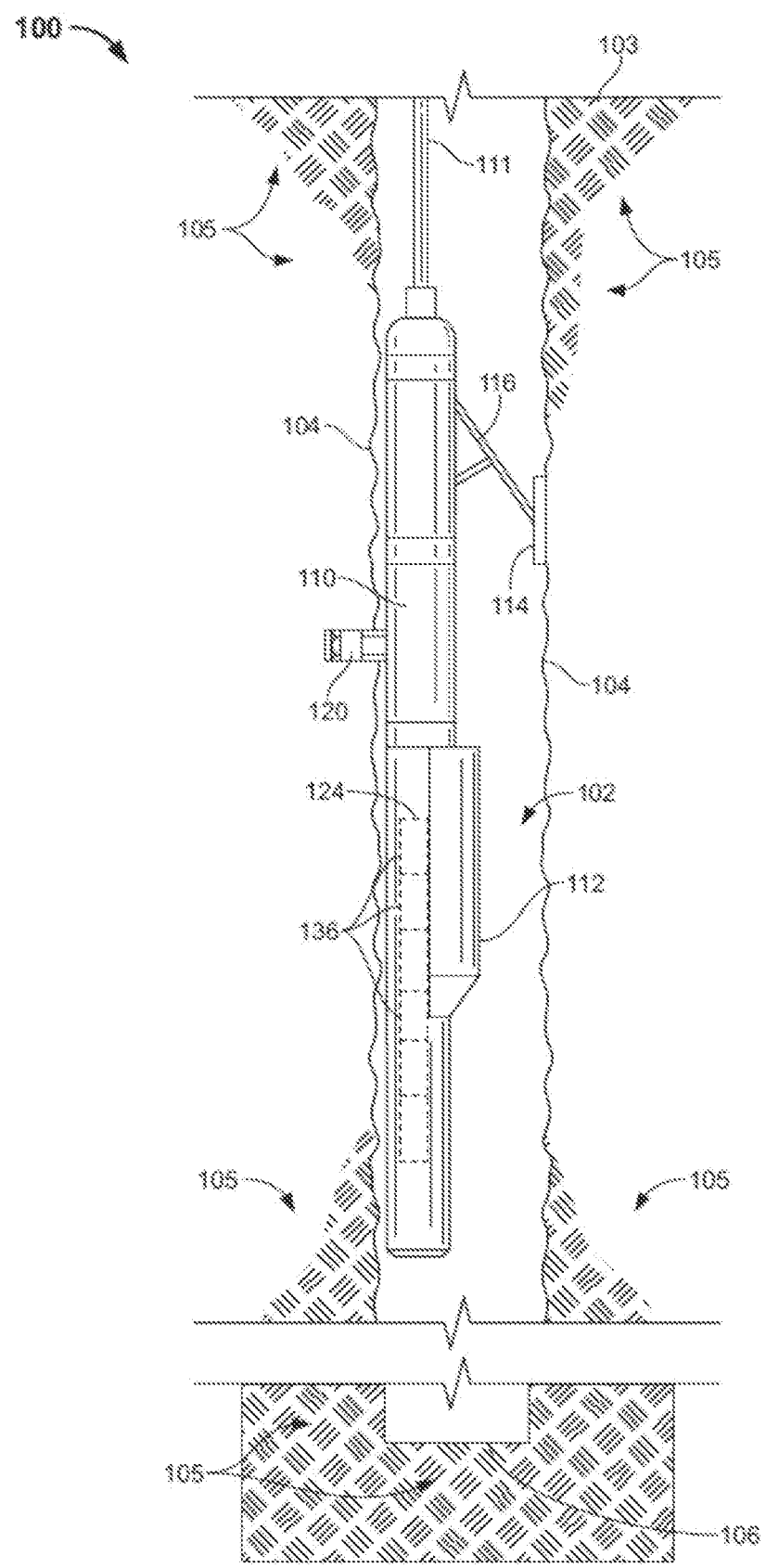
FIGS. 1A and 1B illustrate an example coring tool, according to some embodiments.
Figure 1B:
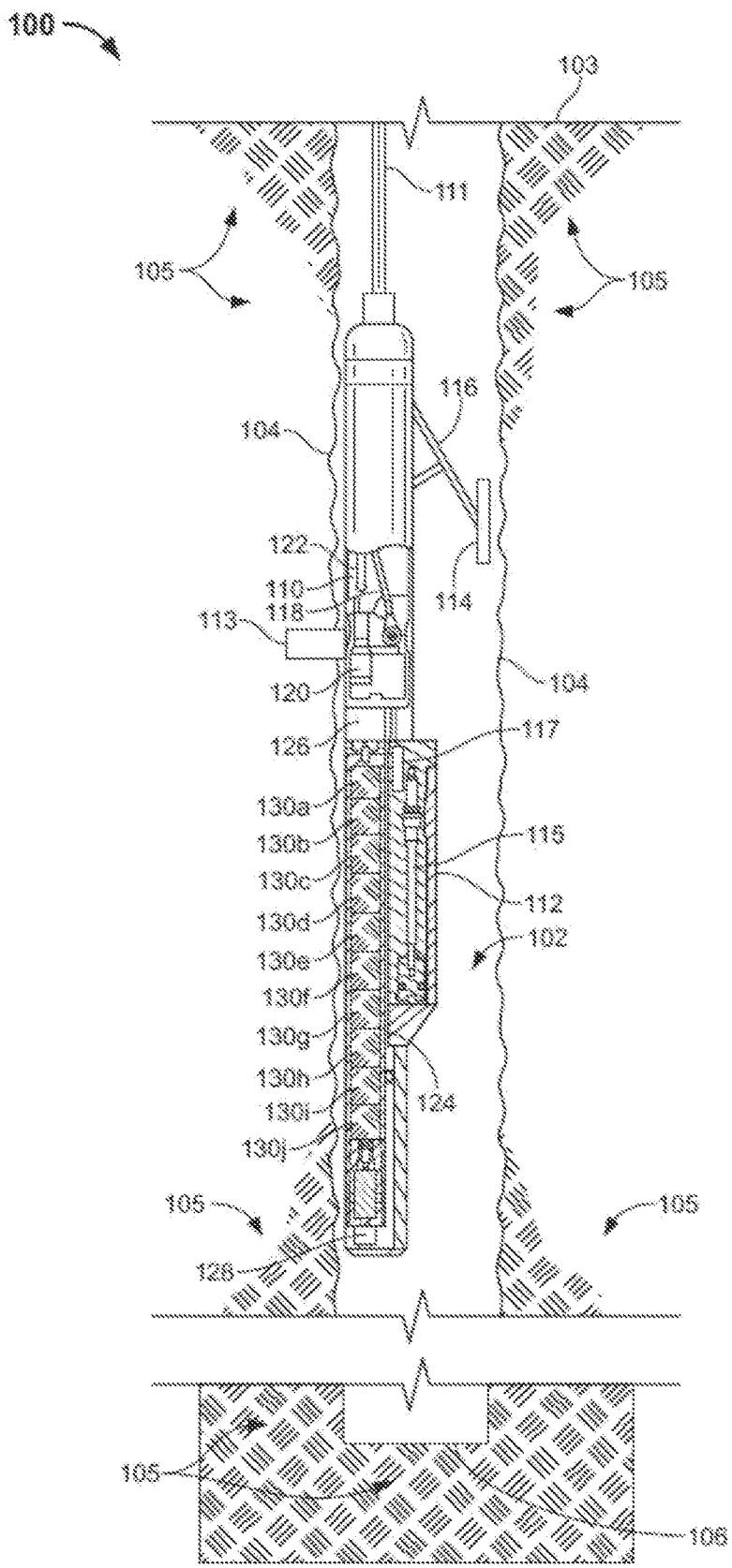

FIGS. 1A and 1B depict a coring tool 100 in accordance with various embodiments. As shown in FIGS. 1A and 1B, coring tool 100 is positioned within a borehole 102 that extends into formation 105 from surface 103, wherein borehole 102 is bounded by borehole sidewalls 104 extending from surface 103 to borehole bottom 106 within formation 105. As shown in FIGS. 1A and 1B, borehole 102 extends in substantially a vertical direction, having a longitudinal axis that is generally perpendicular to surface 103. However, embodiments of coring tool 100 are not limited to being positioned and/or operating in vertically oriented boreholes, and in various embodiments may be positioned and operated in non-vertically oriented boreholes, including slanted or angled boreholes, and/or in portions of a borehole having at least some portion of the longitudinal axis of the borehole that extends in a horizontal direction that is generally parallel to surface 103.

In various embodiments, coring tool 100 includes a sidewall coring section 110, a core receptacle section 112, and a coring stabilizer pad 114. The coring tool 100 may further includes an arm 116 connected to the coring stabilizer pad 114, wherein pad 114 is coupled to the coring tool through arm 116. Arm 116 is adapted to be extended when the coring tool 100 is disposed within borehole 102, thereby displacing the coring stabilizer pad 114 against a portion of borehole sidewall 104 of the borehole, and forcing the sidewall coring section 110 against an opposing borehole sidewall of the borehole. The sidewall coring section 110 includes a bell crank 118, a coring bit 120, and a push rod 122 (shown in FIG. 2B). As shown in FIG. 2B, the bell crank 118 is adapted to displace the coring bit 120 to face the borehole sidewall 104 of the borehole 102 when the stabilizer pad 114 is extended. The bell crank 118 is further adapted to displace the coring bit 120 into the borehole sidewall proximate the formation 105. The coring bit 120 is adapted to cut and detach a core sample of formation 105 from borehole sidewall 104 at the position of the coring bit 120 when the coring bit 120 is displaced by the bell crank 118 and extended into formation 105.

In various embodiments, coring bit 120 includes a finger or other retention mechanism to retain the core sample within the coring bit 120. As shown in FIG. 2B, the bell crank 118 is further adapted to retract the coring bit 120 and the core sample from the borehole sidewall 104, rotate the coring bit including the core sample, and align the coring bit 120 with the core receptacle section 112. The push rod 122 is adapted to extend away from the coring bit 120 when the coring bit 120 is aligned with the core receptacle section 112, thereby pushing the core sample collected by the coring bit out of the coring bit, and depositing the core sample into a pressure vessel 124 positioned within the core receptacle section 112.

In various embodiments, the core receptacle section 112 includes the pressure vessel 124 and a revolving cover mechanism 126. The core receptacle section 112 may also include a chemical chamber 128 adapted to store and/or dispense one or more chemicals (not shown) for use with one or more of the core samples such as core samples 130A-J. The pressure vessel 124 is adapted to receive the core samples 130A-J from the sidewall coring section 110 through a top opening in the pressure vessel 124, wherein in various embodiments the top opening may be selectively opened and closed by the revolving cover mechanism 126. In various embodiments, the pressure vessel is constructed of a pressure resistant metallic alloy and coated with a sulfur inert coating on at least all inner containment surfaces. In this manner, the inner surfaces are resistant to corrosion or other damage that would otherwise be caused by caustic/corrosive substances such as hydrogen sulfide and/or carbonates that may be contained in the core samples. In several exemplary embodiments, the core receptacle section 112 may be a stand-alone assembly adapted for use with another existing sidewall coring tool.

In operation, in various embodiments the coring tool 100 is conveyed to a zone of interest within borehole 102 by a wireline 111 coupled to the coring tool, wherein the wireline may be unwound and/or wound from a wireline spool (not depicted) in order to control the positioning of the coring tool within the borehole. In other embodiments, a tractoring mechanism (not shown) may be used to position the coring tool within the borehole, for example in a portion of a non-vertical section of the borehole. Once it is determined that the coring tool 100 has reached a zone or position within the formation of interest, the coring stabilizer pad 114 is extended such that the sidewall coring section 110 is forced against the sidewall of the borehole 102. The bell crank 118 displaces the coring bit 120 to face the sidewall 104 of the borehole 102. The coring bit 120 is then rotated and displaced into the sidewall of the borehole by the bell crank 118, thereby cutting a respective one of the core samples 130A-J from the sidewall. The resulting respective core sample is detached from the sidewall of the borehole 102 when the coring bit 120 is retracted back into the coring tool 100. Once the coring bit 120 is retracted, the bell crank 118 aligns the coring bit 120 and the respective core sample 130A-J with the top opening of the pressure vessel 124. In various embodiments, before each of the respective core samples 130A-J are deposited into the pressure vessel 124, the revolving cover mechanism 126 may be displaced to a position in which it does not cover the opening of the pressure vessel 124. Alternately, revolving cover mechanism 126 may be positioned so that an opening passing through the revolving cover mechanism aligns with the top opening of the pressure vessel. Once the revolving cover mechanism is properly positioned, each of the respective core samples 130A-j may be deposited into the pressure vessel 124 to form a stack of core samples stored within an inner chamber of the pressure vessel. In various embodiments, chamber seals, as further described below, may be positioned between one or a plurality of the core samples included in the stack of core samples in order to create individually sealed pressure chambers within the pressure vessel. Once the revolving cover mechanism is properly aligned or positioned relative to the pressure vessel 124, the push rod extends from the coring bit, and dispenses the core sample from the coring bit 120, through or past the revolving cover mechanism 126, and into the pressure vessel 124. The push rod is then withdrawn back to the coring bit 120 after having inserted the coring sample fully within the pressure vessel.

Depending on the particular requirements of the sidewall coring operation, the chambers included in the revolving cover mechanism 126 may contain, for example, isolator plugs, swellable packers, discs, packaging film, the cover plug 138, and/or other items for preserving the respective core samples 130a-j, or any combination thereof. Thus, after any one of the respective core samples 130A-J has been deposited into the pressure vessel, one or more of the above listed items may be dispensed into the pressure vessel 124 in order to separate and/or preserve the core samples 130A-J. The above described process may be repeated by displacing the coring tool 100 to other locations within the borehole 102 and collecting another core sample at the each of the new locations. In this manner, the core samples 130A-J may be collected from multiple zones of interest within the borehole 102 and/or from multiple locations within each zone of interest. Once the sidewall coring operation is complete, the push rod 122 seals the pressure vessel 124 with the cover plug 138 and the coring tool 100 is returned to the surface. As depicted and described in further detail below, embodiments of the coring tool may further include pressurization apparatus, such as accumulator 115, adapted for setting and adjusting an internal pressure within pressure vessel 124 that is sufficient to maintain all or most of some gaseous fluid components, such as hydrogen sulfide, within the liquid components of the fluids within the core samples. In some embodiments, the pressurization apparatus may include a nitrogen accumulator configured to provide chemically inert gaseous pressure regulation within the pressure vessel 124.

Having collected the core samples, the pressure vessel 124 may be transported to the surface while maintaining and/or manipulating the pressure within the pressure vessel while the pressure vessel containing the core samples is being removed from the borehole, and after removal of the pressure vessel from the borehole until and/or as part of the testing and analysis of the core samples included in the pressure vessel. For example, once the coring tool 100 has be retrieved to the surface, the pressure vessel may then be removed from the coring tool and shipped to an off-site laboratory for testing and analysis.

In various embodiments, coring tool 100 includes instrumentation 117. Instrumentation 117 is not limited to any particular type of instrumentation, and may include test instruments, such as X-Ray, ultrasonic, NMR, CT and/or gas chromatography test equipment, configured to perform one or more tests on the core samples 130A-J once the core samples have been placed within the pressure vessel and while the coring tool is still positioned downhole within borehole 102. Instrumentation 117 may be communicatively coupled to one or more devices (not shown in FIG. 1A-1B, but see e.g. computer 50, FIG. 8), which are located on the surface, and configured to communicate data, such as test results, to the devices locate on the surface while the coring tool remains positioned downhole within borehole 102. In various embodiments, instrumentation 117 includes a data storage device, such as computer memory (not shown in FIG. but see e.g. memory 1107, FIG. 10), that is configured to store data, such as test result, which may be accessed at a later time, for example when the coring tool has been returned to the surface 103.

FIGS. 1C-1H illustrate various core sampling operations that may be performed by embodiments of a coring tool, such as but not limited to coring tool 100.

Figure 1C:
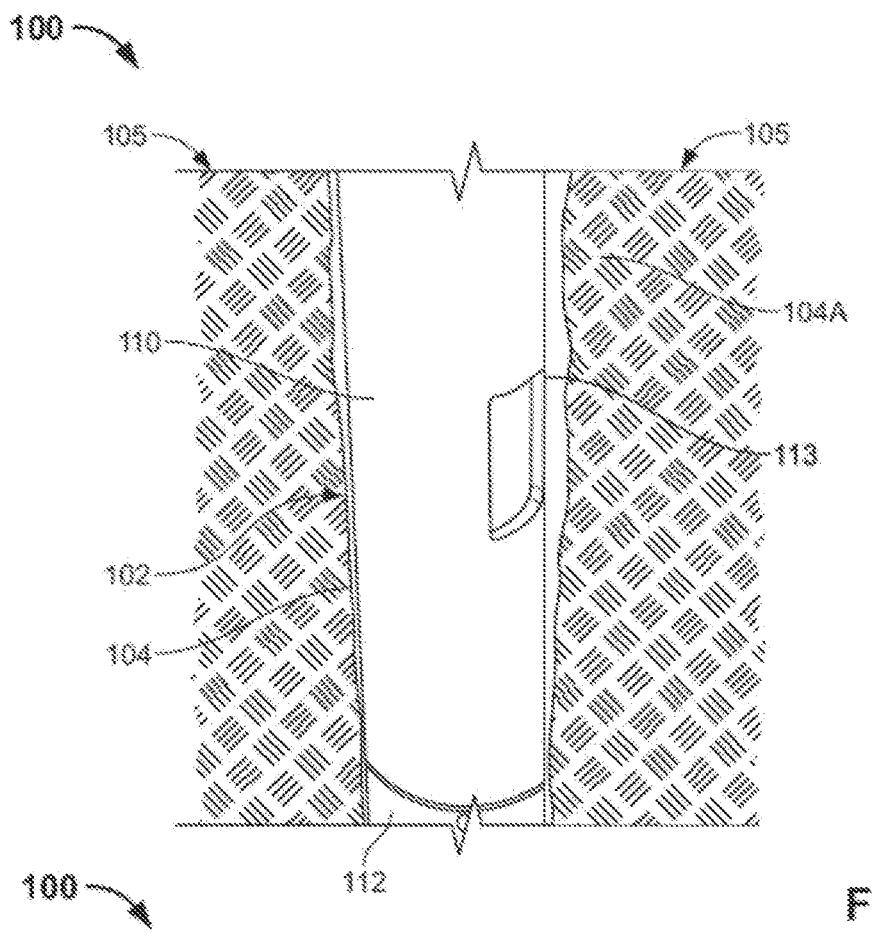
FIGS. 1C-1H illustrate various core sampling operations that may be performed by embodiments of a coring tool.

FIG. 1C illustrates a side view of a portion of coring tool 100 including sidewall coring section 110 positioned within a borehole 102 according to various embodiments. In various embodiments, the positioning of coring tool 100 within borehole 102 may include securing the sidewall coring section 110 against the right-hand side 104A of borehole 102 using an extension arm and a stabilizer pad as described above with respect to FIGS. 1A and 1B. Referring again to FIG. 1C, once coring tool 100 is positioned and secured at a desired location within borehole 102, a coring bit opening 113 extending through the outer surface of the coring tool is thereby positioned proximate to the right-hand side 104A of the borehole at a location within the borehole where a core sample of formation 105 is to be collected.

Figure 1D:
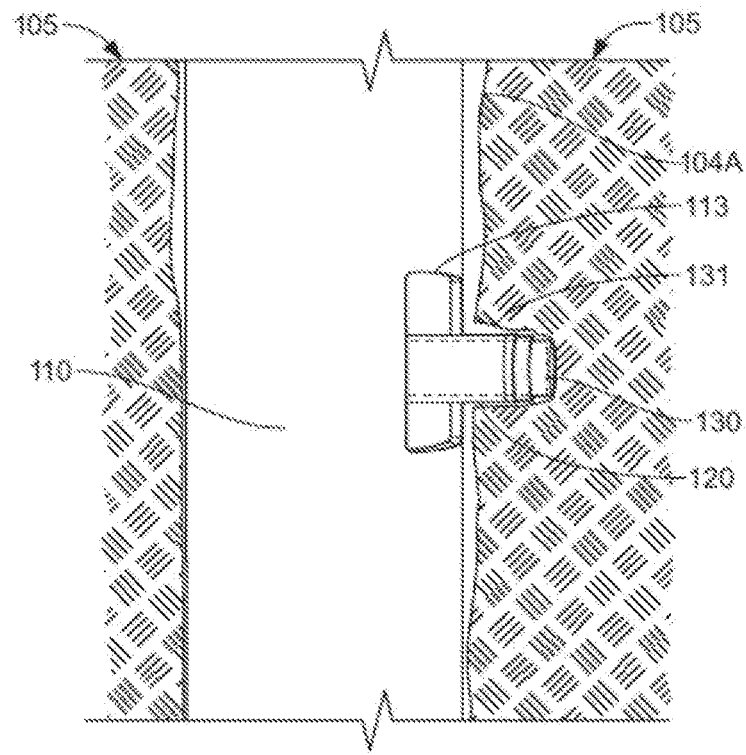

FIG. 1D illustrates the core sampling that may be performed by coring tool 100 following the positioning of the coring tool as illustrated and described with respect to FIG. 1C. As shown in FIG. 1D, the coring bit 120 has been oriented within sidewall coring section 110 so that the coring bit 120 faces borehole sidewall 104A, and extends through coring bit opening 113. The coring bit 120 has further been operated to drill into formation 105 in order to cut a core sample 130 from borehole sidewall 104A, thus creating core sample void 131 extending from borehole sidewall 104A into the formation. Coring bit 120 is further adapted to separate the core sample 130 from the formation material, and retain the separated core sample within the coring bit.

Figure 1E:
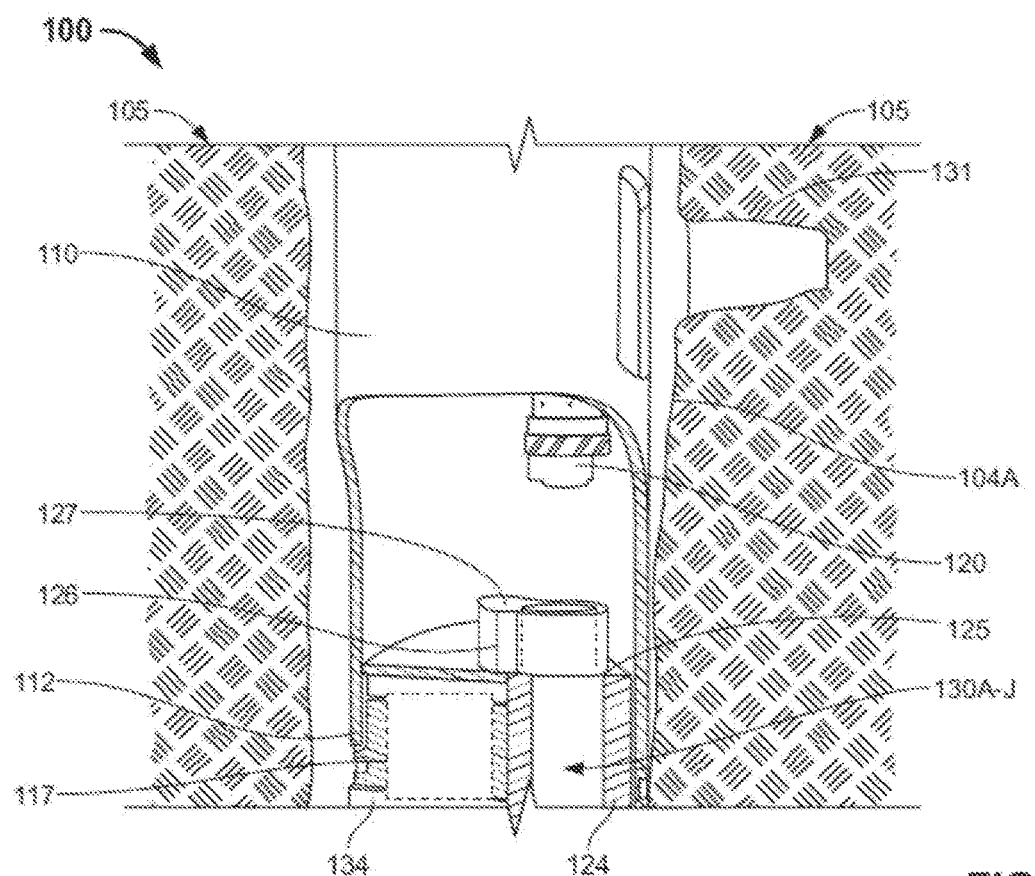

FIG. 1E illustrates a partial cutaway view of coring tool 100, including sidewall coring section 110 and core receptacle section 112, according to various environments. FIG. 1E includes an illustration of the core sampling operations that may be performed by the coring tool following collection of a core sample as illustrated and described with respect to FIG. 1D. As shown in FIG. 1E, the coring bit 120 has been withdrawn back into the coring sidewall section 110, and orientated within the coring sidewall section so that the coring bit faces downward toward a top opening 125 of pressure vessel 124. The coring bit 120 still retains the most recently collected core sample 130, and wherein the coring bit is positioned to align the core sample with an opening 127 extending through the revolving cover mechanism 126 that is also aligned with the top opening 125 of pressure vessel 124.

Figure 1F:
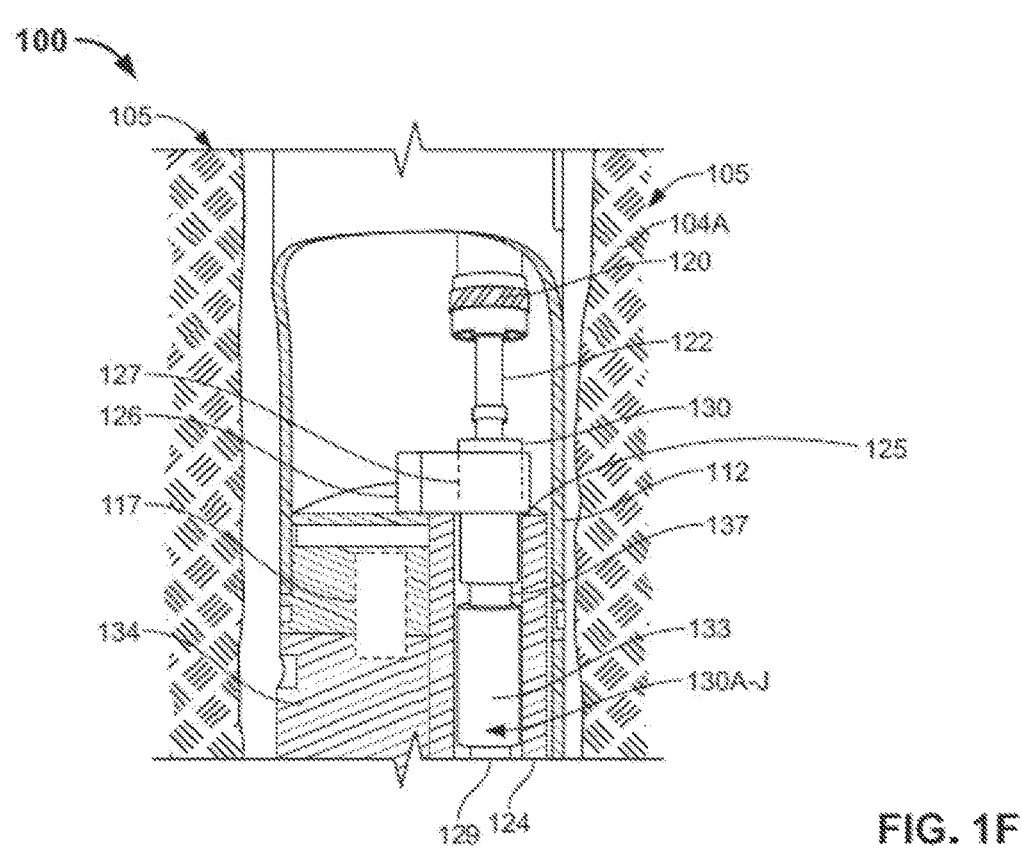
Figure 1G:
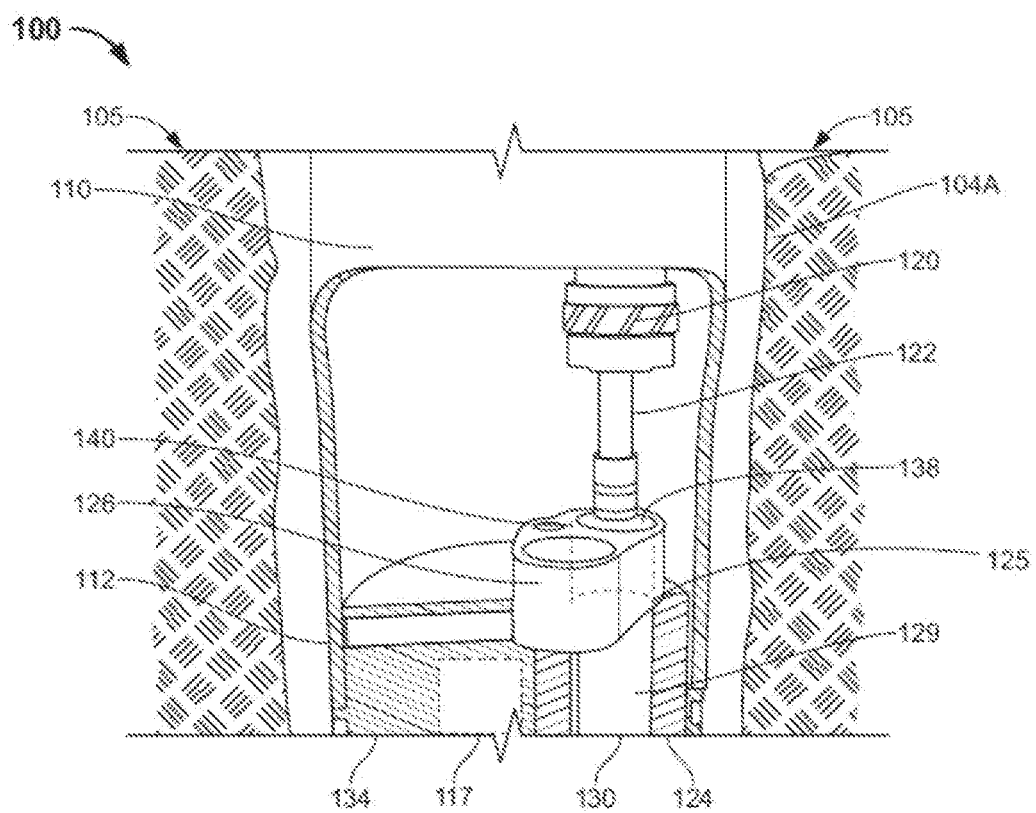

As further illustrated in FIGS. 1E-1G, coring receptacle section 112 may also include instrumentation 117 located within buffer section 134 located adjacent to the pressure vessel 124. Buffer section 134 may include structure, comprising metal and/or plastic, configured to position and hold the pressure vessel 124 in a fixed position with the coring receptacle section 112. In addition, buffer section 134 may include structure configured to position and hold instrumentation 117 in position proximate to the interior chamber 129 of pressure vessel 124. Instrumentation 117 may include any type or types of test and/or analysis equipment configured to perform testing and/or analysis of the core samples that may be collected and located within the pressure vessel, including performing such testing and/or analysis while the core samples and the coring tool 100 remain downhole, and/or on a continual basis as each new core sample is added to the pressure vessel. Instrumentation 117 may include one or more sensors configured to sense and provide an output, such as an electrical output signal, which is indicative of one or more physical parameters, such as pressure levels and/or temperatures, which may be measured within the borehole and/or with respect to the core samples positioned within the pressure vessel.

Sensors included within instrumentation 117 and/or associated downhole and/or surface test equipment may also include gamma ray sensors, nuclear magnetic resonance (NMR) sensors, acoustic sensors, resistivity sensors, other electromagnetic sensors including capacitance sensors or dielectric sensors, optical sensors including spectroscopic sensors such as reflectance sensors or florescence sensors, non optical spectroscopic sensors imaging sensors including resistivity imaging, acoustic imaging and optical imaging sensors, and chemical sensors such as but not limited to mass spectroscopy sensors, chromatography sensors including gas chromatography sensors or liquid chromatography sensors. Mechanical sensors including mechanical rock sensors or fluid PVT sensors may also be included. The sensors may measure rock composition including elemental rock composition, mineral rock composition, rock properties including permeability and porosity, may measure rock mechanical properties or fluid PVT or phase behavior properties. Sensor tests may be performed in replicate at the same or different point, area, or volumetric positions within the core.

The sensors included in instrumentation 117 may be conveyed on multiple platforms and used in a plurality of combinations, those platforms being in line, parallel lines, side branch lines or microfluidic. The sensors may be combined within a single inline measurement direction including same point, or angled to measure simultaneously over an overlapping area or volume of the core. The sensors may directly probe the core sample, or a subsample of the core sample including either rock or fluids contained within the core. The measurement area may be small including micro or nano, or macro including the entire core. The measurement may be bulk volumetric or surface. The sensors may be deployed within instrumentation 117 downhole on or in proximity to the containment pressure vessel 124 that is used as a core containment and transport device. The sensors may also or alternatively be deployed at surface such as in a core containment test vessel, such as depicted in FIGS. 6A-6F into which core samples are transferred such as from pressure vessel 124.

The type of test and analysis equipment included in instrumentation 117 is therefore not limited to any particular type of test or analysis equipment, and may include any of the test and/or analysis equipment described throughout this disclosure, and any equivalents thereof. Any of the information collected by the sensors and/or any of the results determined by the testing/analyses of the core samples using instrumentation 117 may be transmitted using telemetry to a computer device located on the surface, and/or may be stored for example in computer memory, within instrumentation 117 for later retrieval.

FIG. 1F illustrates a partial cutaway view of coring tool 100, including sidewall coring section 110 and core receptable section 112, according to various environments. FIG. 1F includes an illustration of one or more core sampling operations that may be performed by the coring tool following collection of a core sample and retraction of the coring bit 120 as illustrated and described with respect to FIG. 1E. As shown in FIG. 1F, coring bit 120 remains positioned over the opening 127 of the revolving cover mechanism 126 and top opening 125 of pressure vessel 124. A pushrod 122 is extended from the coring bit 120, thus extracting the core sample 130 from the coring bit, and pushing core sample 130 into and through the opening 127 of revolving cover mechanism 126, through top opening 125, and extending at least partially into the interior chamber 129 of pressure vessel 124. Pushrod 122 may be further extended to position core sample 130 completely within the interior chamber 129 of pressure vessel 124.

In various embodiments, prior to extending pushrod 122, a chamber seal 137 may be positioned within opening 127 so that when core sample 130 is received and pushed through opening 127, the bottom surface of core sample 130 pushes the chamber seal out of opening 127 and into the interior chamber 129 of pressure vessel 124, thus separating a previously collected core sample 133 from core sample 130 within the interior chamber of the pressure vessel. One or more chamber seals, such as seals 137, may be positioned within the stack of core samples positioned within interior chamber 129 to create individual chambers (e.g., chambers 136 described above), wherein these individual chambers may be configured to maintain a pressure level within the respective chambers that is not determined by or affected by pressure changes occurring in adjacent chambers within the pressure vessel 124. The use of the chamber seals allows for manipulation of a pressure within a given one of the chambers, for example when removing a core sample or multiple core samples within a given chamber at the surface or otherwise for analysis, while not allowing the change in pressure in the given chamber to have any effect on the pressure(s) being maintained in other chambers within the pressure vessel.

Following the full insertion of core sample 130 within pressure vessel 124, the coring tool 110 may be relocated within the borehole so that core bit 120 is positioned at a new location along borehole sidewall 104, and another core sample may be collected as described above with respect to FIGS. 1C-1F. The number of iterations of positioning the coring tool and collecting a core sample is not limited to a particular number of iterations, and may only be limited by the capacity of pressure vessel 124 to receive a given number of core samples, and associated chamber seals if utilized, within the interior chamber 129 of the pressure vessel.

Figure 1H:
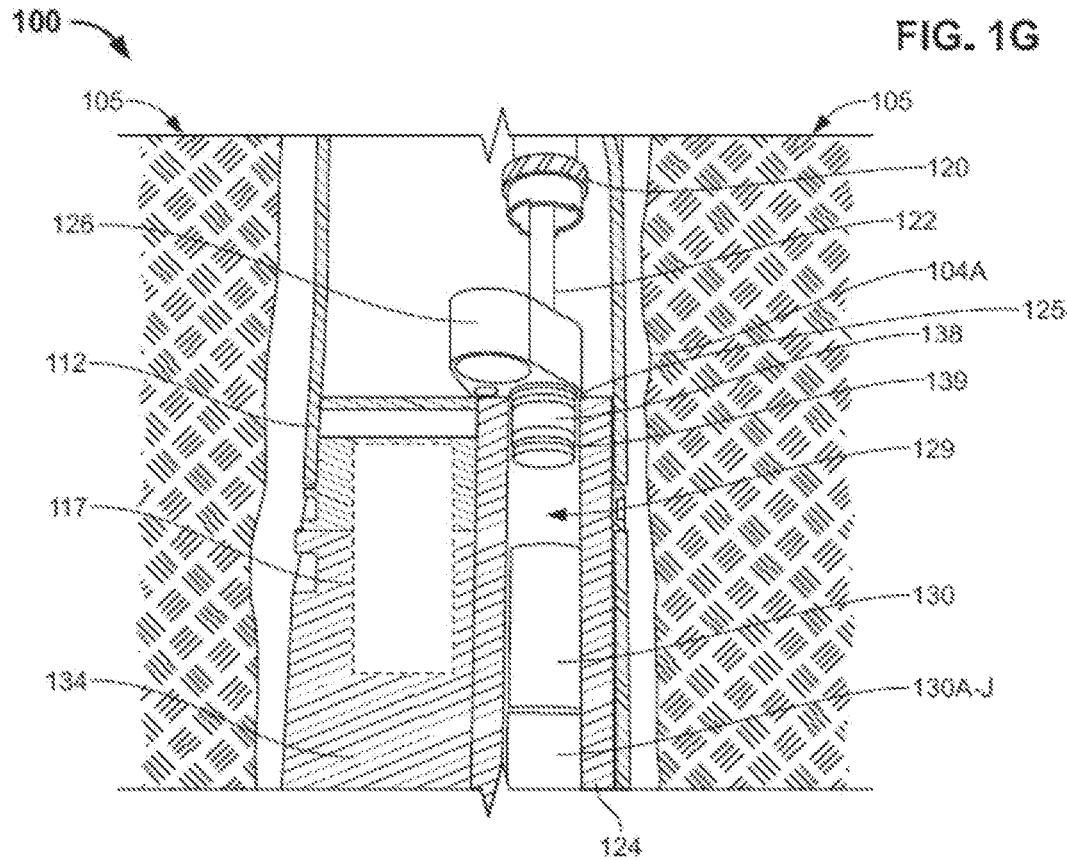

FIGS. 1G and 1H illustrate partial cutaway views of coring tool 100 including sidewall coring section 110 according to various environments. FIGS. 1G and 1H include illustration of the sealing of the pressure vessel 124 following completion of the core sampling operations that may be performed by the coring tool as illustrated and described with respect to FIGS. 1C-1F. In FIG. 1G, following the full insertion of core sample 130 within pressure vessel 124, a cover plug 138, which is positioned in a second opening 140 of revolving cover mechanism 126, is brought into position over the top opening 125 of pressure vessel 124.

As shown in FIG. 1H, cover plug 138 is positioned over top opening 125, pushrod 122 is extended away from coring bit 120 to push cover plug 138 out of second opening 140 and through top opening 125 and fully within interior chamber 129 of pressure vessel 124. A pressure seal 139 positioned within a groove of cover plug 138 is adapted to contact the interior wall surface of pressure vessel 124, and thus create a pressure seal for the interior chamber of the pressure vessel. With cover plug 138 in place within pressure vessel 124, the coring tool 100, including pressure vessel 124, may be retrieved from the borehole 102 to surface 103, while maintaining and/or increasing the pressure within the pressure vessel that was present within the borehole at the time and in the locations were the various core samples now sealed within the pressure vessel were collected. In embodiments where one or more individual chamber seals 137 were incorporated within the stack of core samples contained within the pressure vessel, the chamber seal(s) in conjunction with the cover seal 138 and the accumulator 115 allow for the individual chambers 136 within the pressure vessel to be individually maintained at a desired pressure irrespective of the pressure that is being maintained and/or manipulated in any of the other individual chambers 136.

In various embodiments, revolving cover mechanism 126 may be adapted to be rotated, for example by a rotary actuator, to position the revolving cover mechanism so that it does not cover the top opening of the pressure vessel 124. When positioned so that the revolving cover mechanism 126 does not cover the top opening 125 of the pressure vessel 124, any of the core samples 130A-J may be deposited into the pressure vessel without passing through the revolving cover mechanism. Alternately, revolving cover mechanism 126 may include at least one through passageway, such as opening 127, wherein the revolving cover mechanism may be positioned so that opening 127 aligns with the top opening 125 of the pressure vessel 124, and any of the respective core samples 130A-J may be deposited into the pressure vessel 124 through opening 127. In various embodiments, once the opening 127 is properly aligned or positioned over the top opening of the pressure vessel 124, the push rod 122 dispenses the core sample from the coring bit 120 through and past the opening 127 and into the pressure vessel 124. The push rod 122 is then withdrawn.

In various embodiments, revolving cover mechanism 126 may include a plurality of chambers that may be preloaded with devices that may also be positioned over the top opening 125 of the pressure vessel 124, where these individual devices may be pushed into the pressure vessel using pushrod 122. The rotary actuator may be adapted to rotate the revolving cover mechanism 126 to align a selected one of the chambers with the top opening 125 of the pressure vessel 124. Once aligned with the top opening of the pressure vessel, the device located within the selected chamber may then be dispensed into the pressure vessel 124 by the push rod 122. Depending on the particular requirements of the sidewall coring operation, one or more of the chambers of the revolving cover mechanism may contain, for example, isolator plugs, swellable packers, discs, packaging film, the cover plug 138, other items for preserving the respective core samples 130A-J, or any combination thereof. Thus, after any of the respective core samples 130A-J have been deposited into the pressure vessel, one or more of the above listed items contained in the chambers of the revolving cover mechanism may be dispensed into the pressure vessel 124 in order to separate and/or preserve the core samples 130A-J.

As depicted and described in further detail with for example with reference to FIG. 3 below, the coring tool further includes pressurization means for setting and adjusting an internal pressure within pressure vessel 124 that is sufficient to maintain all or most of some gaseous fluid components such as hydrogen sulfide within the liquid components of the fluids within the core samples. In some embodiments, the pressurization means may include a nitrogen accumulator configured to provide chemically inert gaseous pressure regulation within the pressure vessel 124. Having collected the core samples, the pressure vessel 124 is transported to the surface and can then be removed from the coring tool 100 and shipped to an off-site laboratory for testing and analysis.

Figure 2:
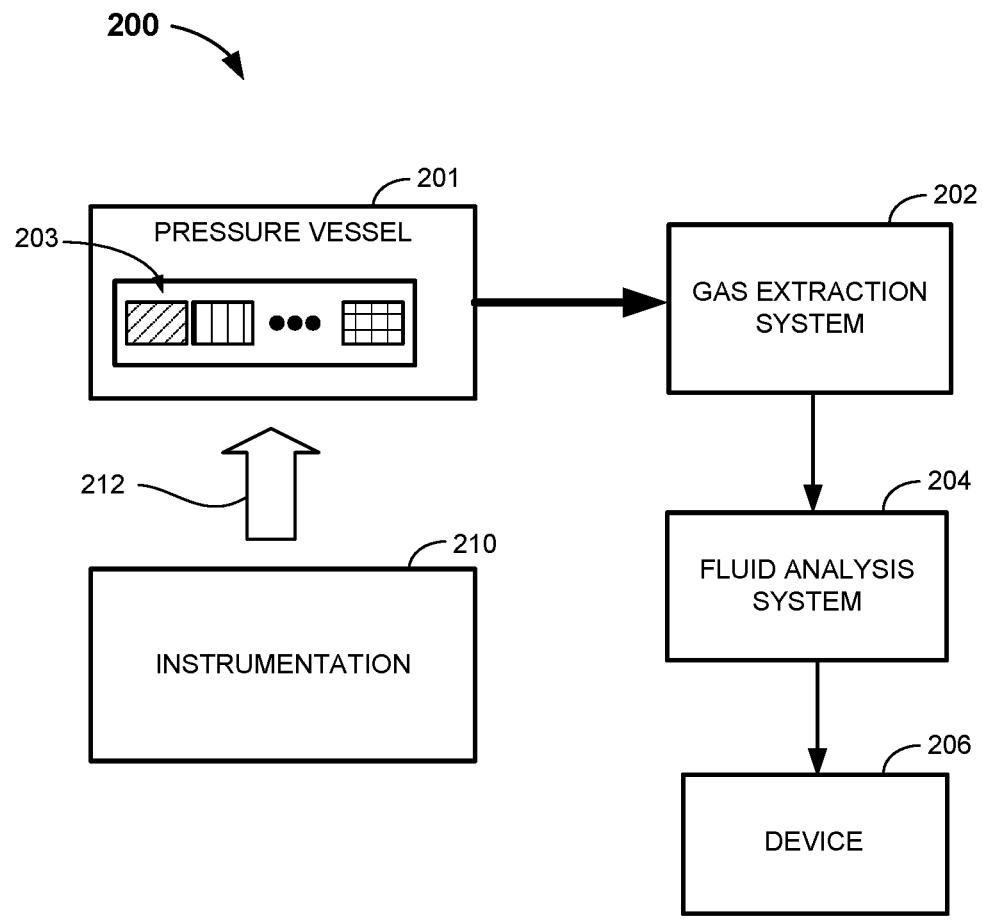
FIG. 2 is a block diagram of an example system for core sampling and gas extraction and analysis, according to some embodiments.

FIG. 2 depicts an example system 200 for core sample analysis, and gas extraction and analysis, according to some embodiments. System 200 includes a gas extraction system 202, a fluid analysis system 204, and a device 206. A pressure vessel 201 that contains one or more core samples 203 is coupled to an input port of the gas extraction system 202. Pressure vessel 201 may include any of the embodiments of pressure vessels described throughout this disclosure, and any equivalents thereof. The core samples 203 may be core samples that have been collected by any of the embodiments and/or core sampling tools described throughout this disclosure, and any equivalents thereof. Upon completion of the collection of the core samples 203 and placement of the core samples within the pressure vessel 201, pressure vessel 201 may be sealed in order to maintain the pressure levels present within the pressure vessel while the pressure vessel remains downhole. In addition, one or more devices, such as apparatus 115 as illustrated and described above with respect to FIG. 1B, may be coupled to the pressure vessel 201 and configured to maintain the pressure level(s) within the pressure vessel as the pressure vessel, including core samples 203, is retrieved from a downhole location to the surface of the borehole. The apparatus may also be configured to provide compensation for pressure changes that may occur within the pressure vessel due to temperature changes occurring within the pressure vessel.

In operation, the pressure that has been maintained within the pressure vessel 201 may be released into a collection chamber within the gas extraction system 202, enabling a controlled pressure drop in the sealed vessel, and gases contained within one or more of the core samples 203 to come out of solution and be released into the collection chamber. System 200 may be configured release pressure from a single and isolated one of the core samples 203 included in pressure vessel 201, and to subsequently repeat the pressure and gas release process with each individual core sample separately and in sequence. Alternatively, the core samples within the pressure vessel may be de-pressurized and the gas extracted from all of the core samples 203 as a whole and in a single de-pressurizing operation.

An output of the fluid extraction system 202 is coupled to the fluid analysis system 204, which as a non-limiting examples may include a gas chromatograph that is configured to measure or otherwise determine concentrations of species based on the extracted fluid and/or gas received from fluid extraction system 202. The fluid analysis system 204 may be configured to determine concentration of each species of the extracted gas over time. In various embodiments, the fluid analysis system 204 is configured to determine chemical species of gases extracted from the one or more core samples 203 that include hydrogen sulfide and carbonates such as carbon dioxide. The fluid analysis system 204 may be further configured to determine chemical species such as methane, ethane, propane, isobutane, butane, isopentane, and pentane.

The device 206 is coupled to receive values of the concentration of each species of the extracted gas over time from the fluid analysis system 204. The device 206 can by any combination of hardware, software, firmware, etc., configured to perform the operations described herein. For example, the device 206 may include a processor configured to execute program code stored on a machine-readable medium also included in device 206, such as the computer system 1100 illustrated and described below with respect to FIG. 11.

In addition to the testing/analysis performed by the fluid analysis system 204, embodiments of system 200 may include instrumentation 210 positioned adjacent to pressure vessel 201. Instrumentation may include one or more types of test and/or analysis devices, which are configured to perform one or more types of testing on the core samples 203 while the core samples are positioned within pressure vessel 201. In various embodiments, instrumentation 210 may be instrumentation 117 as illustrated and described for example in FIGS. 1E-1H, and may be configured to perform any of the functions ascribed to instrumentation 117. In various embodiments, instrumentation 210 may be instrumentation 600 as illustrated and described for example in FIGS. 6A-6H, and may be configured to perform any of the functions ascribed to instrumentation 660. In various embodiments, some or at least a portion of pressure vessel 201 comprises a material, such as a metal, a plastic, or a composition such as fiberglass, that allow for various types of testing to be performed on the core samples 203 while the core samples remain in the pressure vessel.

Figure 3:
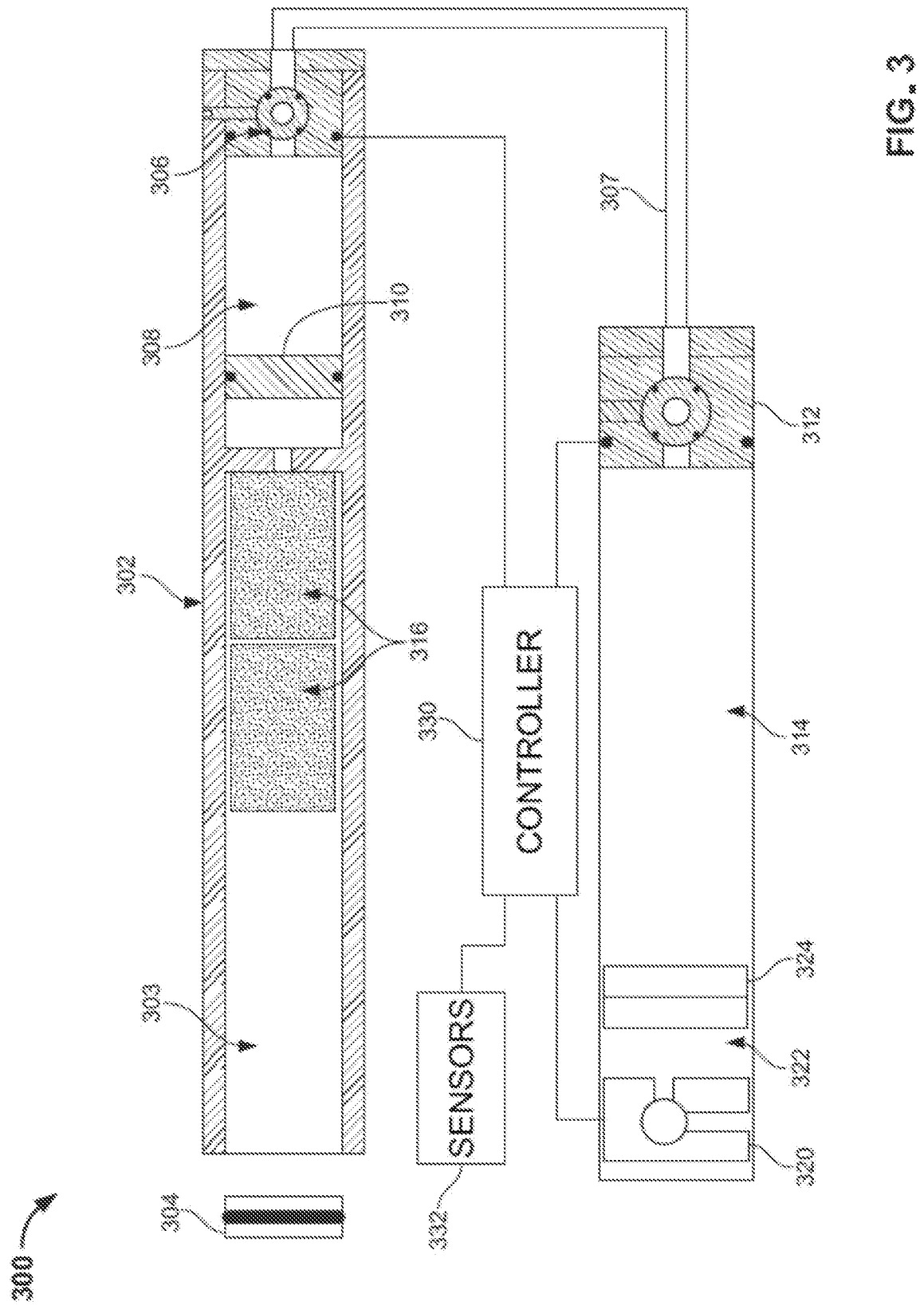
FIG. 3 illustrates a coring tool that includes a nitrogen accumulator for pressure and temperature compensation, according to some embodiments.

FIG. 3 depicts a coring tool 300 that includes a nitrogen accumulator for pressure and temperature compensation, according to some embodiments. A coring tool 300 includes a core barrel or pressurized vessel 302 having a core chamber 303 configured to house the cores samples 316 in a pressurized environment after extraction from a formation. The coring tool 300 includes a sealed cap 304 configured to be positioned over an opening of the core chamber 303 after the core samples 316 have been placed in the core chamber 303. A sealed piston 310 is positioned in the core barrel 302 adjacent to the core chamber 303 at the opposite end of the opening where the sealed cap 304 is placed. A nitrogen chamber 308 includes nitrogen ($N_2$) pre-pressurized gas and is positioned adjacent to the $N_2$ sealed piston 310 and opposite of the core chamber 303. While described in reference to nitrogen, example embodiments can include other types of gases. For example, any other type of inert gas (such as argon, neon, etc.) can be used.

The coring tool 300 includes a controllable gas valve 306 positioned at an inlet of the $N_2$ chamber 308. The coring tool 300 includes a controllable gas valve 312 positioned at an outlet of a high pressure gas reservoir 314. Valves 306 may be coupled to value 312 through fluid conduit 307. The valves 306 and 312 can be controlled to enable use of the gas, such as nitrogen, in the reservoir 314 to increase or maintain the pressure in the core chamber 303. For example, the valves 306 and 312 can be controlled by a controller or processor (330) at the surface and/or downhole. To enable the use of the gas (for example nitrogen) contained in the reservoir 314, the valves 306 and 312 can be opened to allow the gas to flow into the $N_2$ chamber 308 to increase or maintain the pressure in the core chamber 303 via the $N_2$ seal piston 310. As the coring tool 300 is brought to the surface, the nitrogen expands, thereby increasing the pressure on the cores 316. Thus, example embodiments can include surface control of a nitrogen accumulator system using electronic valve control to initiate a pressure compensation system.

In various embodiments, a pressure piston 324 may be positioned near one end of the high pressure gas reservoir 314, creating a space 322 between the pressure piston and a gas valve 320 located at the end of the vessel containing the high pressure gas reservoir. The pressure piston 324, space 322, and gas valve 320 may operate as a pressure relief system to allow for expansion, and in certain situations, venting the pressure within space 322 through gas value 320, to prevent and/or control the level of pressure present in the high pressure gas reservoir 314. The pressure piston 324, space 322, and gas valve 320 may operate as a control mechanism to control the overall pressure within the reservoir 314 by controlling the addition and/or venting of an outside pressure source provided to valve 320 which may be regulated to control the pressure level within space 322, and thus also within the high pressure gas reservoir 314. Control of the operation of any of the gas valves included in coring tool 300, and the overall operation of the coring tool 300, may be controlled by outputs provided to the valves by controller 330, and may be based, at least in part, on input signals generated by one or more sensors 332 and communicated to the controller.

Some embodiments of coring tool 300 can include real-time surface monitoring of the coring tool 300 and hydrostatic pressure-temperature data utilizing active sensors (332) and borehole telemetry. Additionally, some embodiments can include a high-pressure nitrogen accumulator with surface pressure readout and electronic valve control. Embodiments of coring tool 300 may be utilized to maintain predetermined pressure levels within a pressure vessel, such as pressure vessel 302, while the pressure vessel is being used to store core samples downhole, and during the retrieval and subsequent handling of the pressure vessel from downhole to the surface of the borehole.

Reservoir hydrocarbon physical properties can provide important and essential parameters for hydrocarbon production forecasting and reservoir performance. One such parameter is the oil saturation (bubble point) pressure. The bubble point can be defined as the pressure at which gas begins to break out of an undersaturated oil and form a free gas phase in the host rock matrix. Some embodiments include operations to determine bubble point pressure through system compressibility measurements of the sealed pressure vessel. Such operations can yield important reservoir properties particularly associated with organic-rich mudstone "shale" reservoirs.

Figure 4:
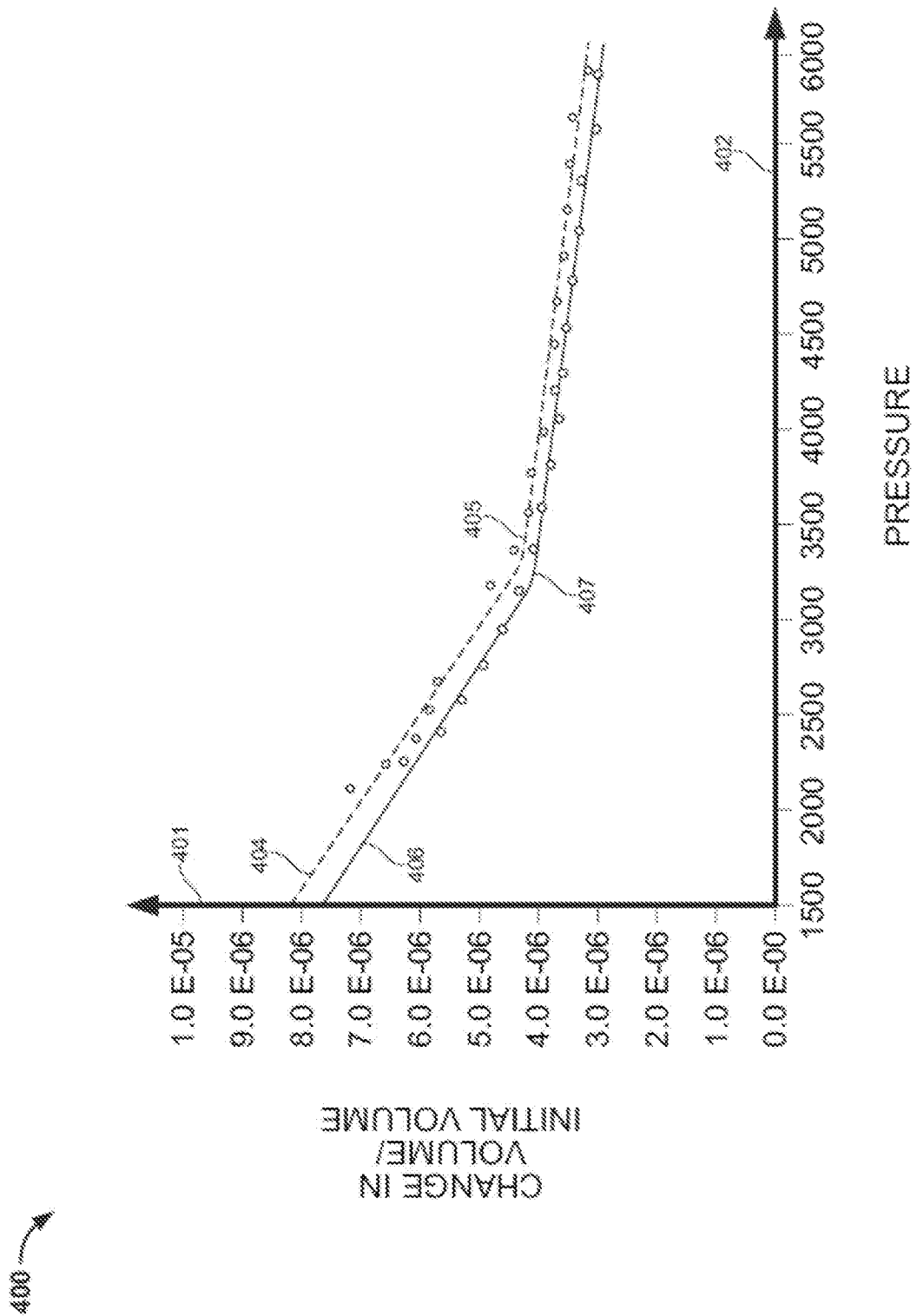
FIG. 4 illustrates an example graph of fit compressibility data to find a bubble point.

FIG. 4 depicts an example graph 400 of fit compressibility data to find a bubble point. Different hydrocarbons can have different bubble points. Thus, the bubble point can be an important parameter in estimating the hydrocarbon recovery from a formation. Graph 400 includes a y-axis 401 which is a unitless change in volume versus initial volume, and an x-axis 402 which is in units of pressure in pounds-per-square inch (PSI). A core sample can be extracted from a subsurface formation and stored in a pressurized vessel. The core sample can include a solid, a liquid and a gas. Example embodiments apply a pressure on the core sample in the pressurized vessel (using operations described herein). The applied pressure is such that the pressure remains above a bubble point pressure for the core sample. The pressure applied to the core sample remains above the bubble point pressure even while the core sample is brought to the surface and to a lab to be analyzed. Thus, the gas remains in the fluid of the core sample. At the surface, a compressibility analysis on the total composition of the core sample can be performed to determine its bubble point. Thus, the bubble point pressure can be accurately determined.

In graph 400, lines 404 and 406 represent a fit of the data points associated with a pressure of a confidence bounds e.g. 3499 psi to 3101 psi, as determined by the intersection of upper bound of the two lines and lower bound of the two lines. Line 404 includes inflection point 405, and line 406 includes inflection point 407. The upper and lower bounds of the four lines may be determined at the 95% confidence interval. The intersection of an upper trend and lower trend line represents the bubble point. In graph 400, there are four such intersections. The intersection of the upper and lower bounds at a 95% confidence interval does not correspond to the 95% confidence interfile of bubble point. In general, the confidence bands are solved numerically by Monte Carlo simulation.

Figure 5:
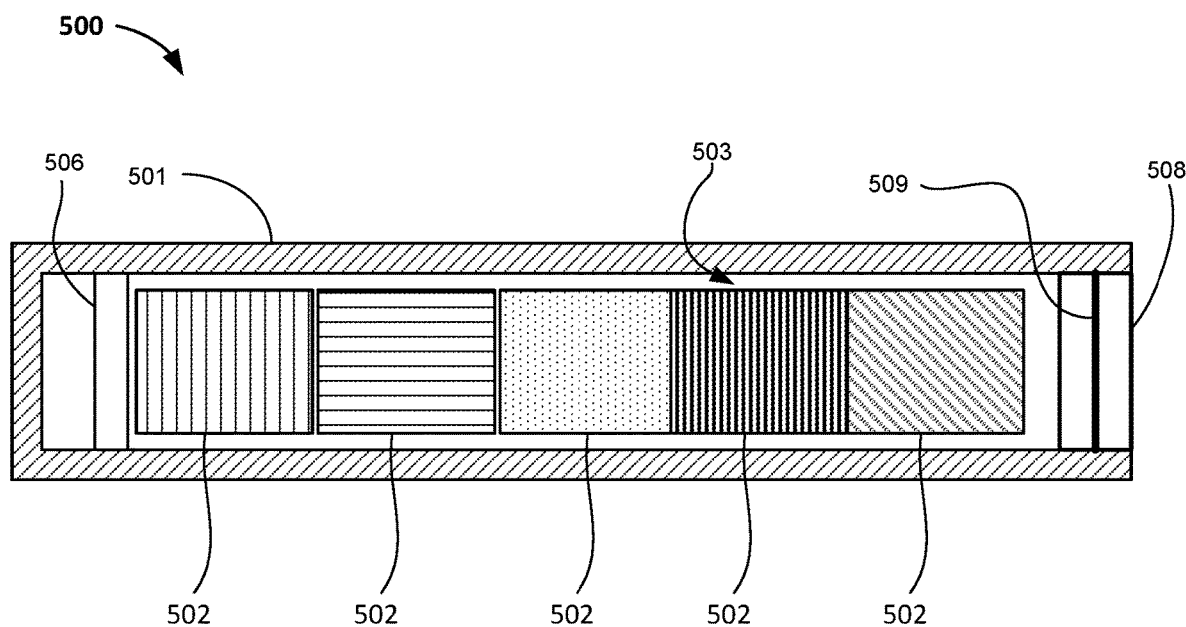
FIG. 5 illustrates an example pressurized vessel that includes NMR and CT transparency, according to some embodiments.

FIG. 5 depicts an example pressure vessel 500 formed at least in part from a material that includes Nuclear Magnetic Resonance (NMR) and Computed Tomography (CT) transparency, according to some embodiments. The pressure vessel 500 includes an interior chamber 503 enclosed at least partially by vessel walls 501. The interior chamber 503 is configured for storing the one or more core samples 502 while having the area within the interior chamber and surrounding the core samples pressurized to some pressure level. In various embodiments, the pressure vessel is configured to contain pressures above ambient pressure in the range of 0.01 (vacuum) to 45,000 pounds/square inch (PSI). Pressure vessel 500 may include at least one open end that may be pressure sealable by a piston or seal 508 including a pressure seal 509 that is configured to contact the inner surface of the interior chamber and maintain a pressure level in the area surrounding the core samples 502. In various embodiments, the stack of core samples may include a second pressure sealing piston 506 positioned an end of the stack of core samples 502, the sealing piston 506 also configured to provide a pressure seal to maintain the pressure level in the area surrounding the core samples 503.

Pressure vessel 500 may be composed of a high tensile strength material, such as steel. In various embodiments, the pressurized vessel 500 be composed, at least in part, of a nickel, chromium, cobalt alloy. However, in some embodiments, the pressurized vessel is composed to provide for NMR and CT transparency to allow for NMR and CT scanning of the core samples that are within the pressurized vessel. In some embodiments, at least a portion of the pressurized vessel is composed to provide for NMR and CT transparency. A number of core samples 502 are stored in an NMR and CT transparent pressurized vessel 500. For example, at least a portion of the pressurized vessel 500 can be composed of PEEK, fiberglass, etc. In one example, the entire pressurized vessel is composed of a material to allow for NMR and CT transparency. In another example, one or more windows can be formed in the pressurized vessel 500 that allows for NMR and CT transparency.

Accordingly, NMR and CT scanning can be performed while the core is still pressurized in the pressurized vessel. Important fluid volume, fluid typing and identification, and pore size distribution can be determined through NMR and CT scanning of the core within the pressurized vessel. In addition, dual-frequency NMR experiments can be performed to identify both hydrogen and fluorine proton resonance of the core sample. Thus, NMR and CT measurements of sidewall core physical properties would be conducted at reservoir pressure conditions. In an application, NMR or CT scanning can be performed on the core sample in the pressurized vessel during the pressure reduction of the pressurized vessel.

Example embodiments can include pressure vessel 500 configured to be removed from a coring tool and inserted into a core sample testing system. The core samples sealed in the pressurized vessel of the coring tool (still under a high pressure) can be transferred to laboratory test cells on an individual core sample basis. In these example embodiments, the core sample testing system may be configured so that there is no or little loss or decrease in pressure in the area surrounding the core samples 502 during this sealed pressure core transfer. Once the core samples are transferred, physical rock and reservoir properties can be determined using various testing methods (including NMR, CT and triaxial rock mechanics testing, and including any of the testing and analysis techniques described herein, and any equivalents thereof.

Figure 6A:
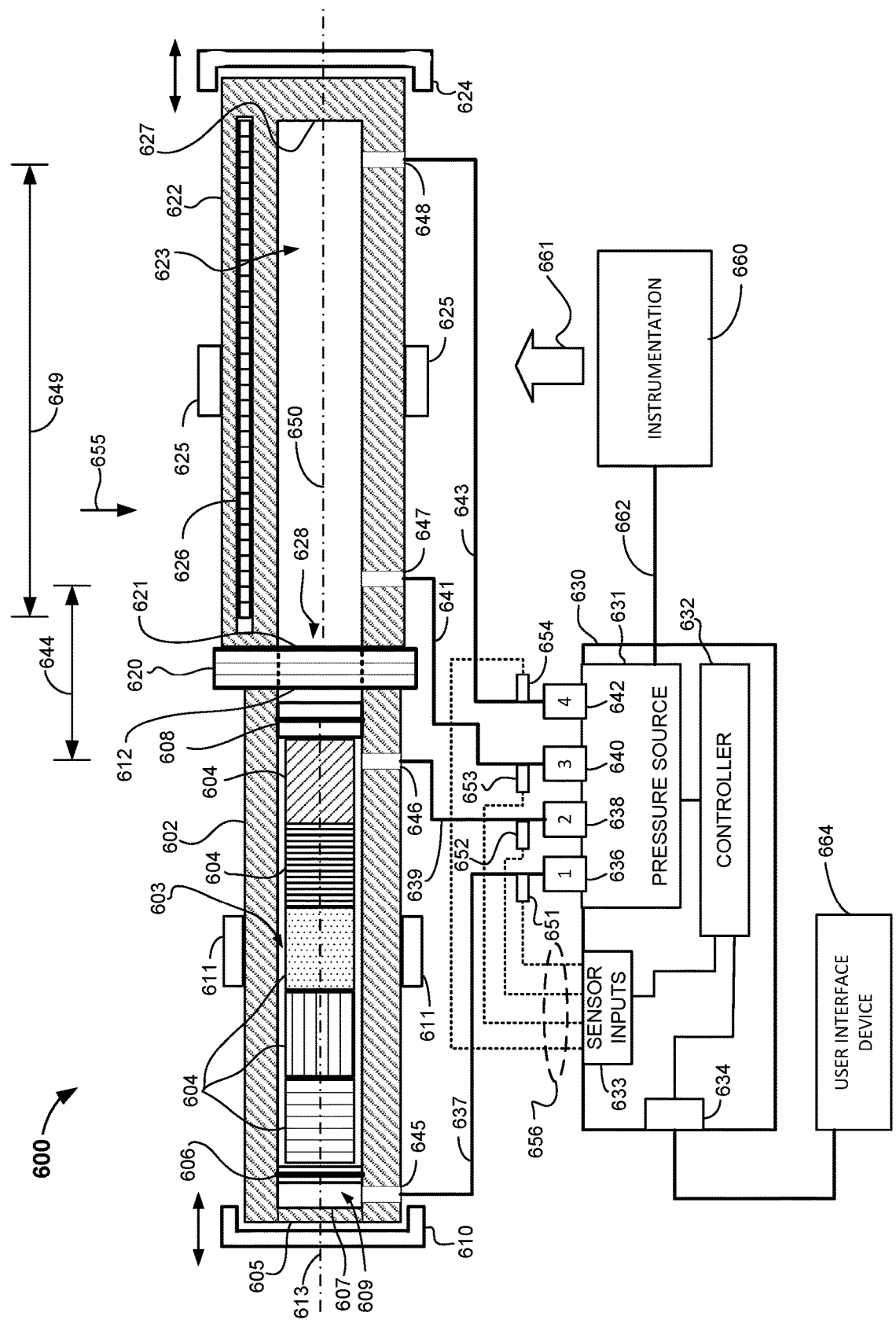
FIGS. 6A-6B illustrate an example pressure core seal transfer system, according to various embodiments.
Figure 6B:
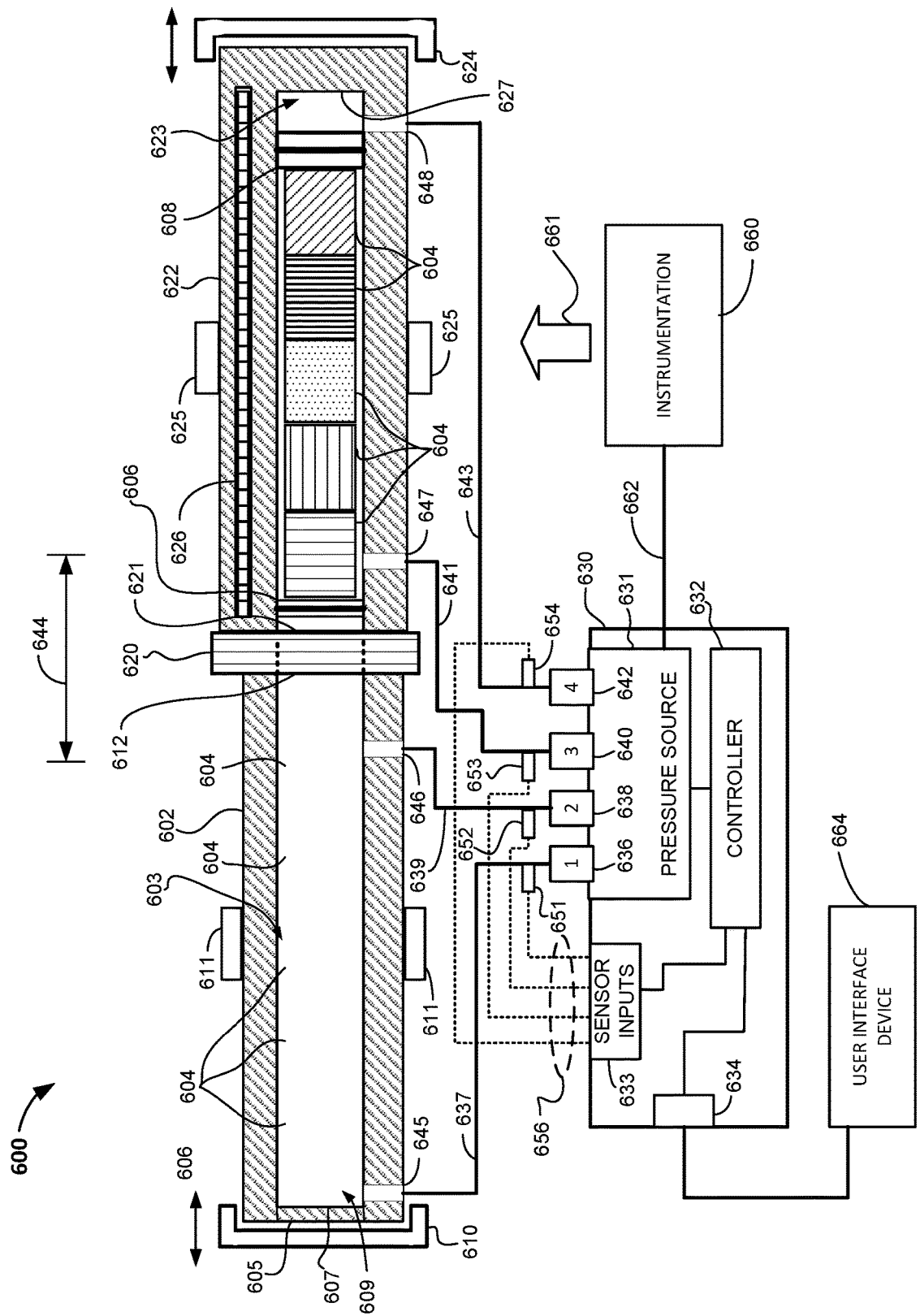

FIGS. 6A-6B illustrate a core sample transfer system 600 according to various embodiments. As shown in FIG. 6A, system 600 includes a pressure vessel 602, a lab vessel 622, and a pressure control system 630. Pressure vessel 602 may be part of the coring tool, such as pressure vessel 124 of coring tool 100 as illustrated and described with respect to FIG. 1. FIG. 6A illustrates a cut-away view of pressure vessel 602, including the pressure vessel walls formed as a hollow cylindrical shape that encircles an interior chamber 603 extending along a longitudinal axis 613. In various embodiments, a bottom plug 605 seals off a bottom end 607 of the interior chamber 603 of pressure vessel 602. The end of pressure vessel 602 opposite the bottom end 607 includes a top opening 612. Top opening 612 may provide an access opening that extends from internal chamber 603 to areas outside the walls of pressure vessel 602. Top opening 612 provides access though which core samples, such as core samples 604 as illustrated in FIG. 6A, may be inserted for example by a coring tool such as coring tool 110 (FIG. 1) into the interior chamber 603 of the pressure vessel. As illustrated in FIG. 6A, the interior chamber 603 of pressure vessel 602 has been loaded with five individual core samples 604, each of the core samples 604 having an upright cylindrical shape and stacked together along the longitudinal axis 613 of the interior chamber 603 of the pressure vessel, having an end of each core sample adjacent to an end of another core sample. The number of individual core samples included in embodiments of the pressure vessel 602 is not limited to five core samples as illustrated in FIG. 6A, which is merely an illustrative example, and may include more or less core samples. The total number of core samples that may be included in various embodiments of pressure vessel 602 may be limited by the total capacity of the core samples that may be included within interior chamber 603, allowing for additional space taken up by any pistons and/or sealing devices that may need to be included as part of the pressure packaging for core samples within the pressure vessel. In various embodiments, the core samples may have a diameter in cross section of approximately ¼ inch and may have a length along the longitudinal axis 613 in a range from 6 to 24 inches, inclusive.

In various embodiments, at the end of the stack of core samples 604 nearest the bottom plug 605, an end piston 606 may be positioned between an end of the stack of the core samples and the bottom plug, wherein the positioning of the end piston within the interior chamber 603 allows for an interior space 609 within the interior chamber between the bottom plug and the end piston. End piston 606 may include a sealing element, such as an O-ring, having a perimeter surface that is in contact with the interior surface wall of the interior chamber 603, the sealing element forming a pressure seal to allow for pressure differences to be maintained on opposite sides of the end piston. A pressure within the interior space 609 may be controlled through pressure port 1 (645) by pressure control system 630 as further described below. In various embodiments, end piston 606 may be configured as a lockable/releasable piston that may be locked in place with the interior chamber 603 and released to allow movement of the end piston along the longitudinal axis of the pressure vessel 602 while still maintaining a pressure seal against any pressure differences that might exists on opposite sides of the end piston. This feature allows for repositioning the end piston 606 within interior chamber 603, and in various examples, allows moving end piston 606 out of the pressure vessel 602 through top opening 612 and into an interior chamber 623 of the lab vessel 622, as further described below.

In various embodiments, a top seal 608 may be positioned at the end of the stack of core samples 604 nearest the top opening 612, between the top opening 612 and an end of the stack of the core samples opposite the end of the core stack proximate to end piston 606. The positioning of the top seal 608 within the interior chamber 603 allows for sealing a pressure (or multiple pressures) that may be present within the area of interior chamber 603 that includes the core samples to be maintained relative to any pressure differential that may be present in the area within the interior chamber between the top seal 608 and top opening 612. In various examples, a pressure or pressures that may be present within the area of interior chamber 603 that includes the core samples may have been present at the time the core samples 604 were collected downhole as part of a core sampling operation. These pressure(s) may have been further maintained or adjusted within the pressure vessel 602 for example by a pressure control system and/or an accumulator, such as included in the embodiment of coring tool 300 as illustrated and described with respect to FIG. 3.

Referring again to FIG. 6A, in various embodiments top seal 608 may have been positioned within interior chamber 603 as a finishing step in completing a core sampling operation, and performed while the coring tool, including pressure vessel 602, remains downhole and at the same or similar downhole pressures within the borehole that were present where the core samples were collected. Top seal 608 may include a sealing element, such as a O-ring, having a perimeter surface that is in contact with the interior surface wall of the interior chamber 603, the sealing element forming a pressure seal to allow for pressure differences to be maintained on opposite sides of the top seal. A pressure within the area of interior chamber 603 that includes the core samples may be controlled through pressure port 2 (646) by pressure control system 630 as further described below. In various embodiments, top seal 608 may be configured as a lockable/releasable piston that may be locked in place within the interior chamber 603, and released to allow movement of the top seal 608 along the longitudinal axis of the pressure vessel 602 while still maintaining a pressure seal against any pressure differences that might exists on opposite sides of the top seal. This feature allow for repositioning of the top seal 608 with interior chamber 603, and in various examples movement of the top seal 608 out of the pressure vessel 602 through top opening 612 and into the interior chamber 623 of the lab vessel 622, as further described below.

FIG. 6A includes a cut-away view of lab vessel 622, including the lab vessel walls formed as a hollow cylindrical shape that encircles an interior chamber 623 extending along a longitudinal axis 650. As shown in FIG. 6A, top opening 612 of pressure vessel 602 is coupled to a top opening 621 of lab vessel 622 through a pressure seal 620. Pressure seal 620 incudes a passageway 628 extending through the center portion of the pressure seal, the passageway having a shape and interior dimensions that allow any core samples, such as core samples 604, and any pistons and/or top seals including in or around the stack of core samples, to pass through this passageway in order to allow transfer of one, some, or all of the core samples positioned within the pressure vessel 602 to the interior chamber 623 of the lab vessel. The passageway 628 further allow for transfer of these same core sample(s) back into the pressure vessel from the lab vessel. As shown in FIG. 6A, lab vessel 622 includes a pressure port 3 (647) located near top opening 621 of the lab vessel, and a pressure port 4 (648) located near a bottom end 627 of the lab vessel. Each of pressure ports 3 and 4 are coupled to a controllable pressure output provided by pressure control system 630 and are in fluid communication with the interior chamber 623. Control of the pressure provided to pressure ports 3 and 4 may be performed as part of a process used to transfer core sample(s) from the pressure vessel 602 into the interior chamber 623 of the lab vessel, and/or to transfer core samples back into the pressure vessel from the lab vessel.

Pressure seal 620 is configured to provide a pressure tight seal between the interior chamber 603 of pressure vessel 602 and the interior chamber 623 of lab vessel 622 when the pressure vessel and the lab vessel are positioned so that the top opening 612 and top opening 621 are aligned and joined together by mutual sealing contact with pressure seal 620. In order to achieve and maintain the proper alignment and sealing position required to maintain the desired arrangement of pressure vessel 602 relative to lab vessel 626, one or more types of fixturing may be provided. By way of non-limiting example, a fixture 610 may be positioned to enclose a portion of the pressure vessel 602, including the bottom end of the pressure vessel. Fixture 610 may be movable, for example in a direction parallel to a longitudinal axis of pressure vessel 602, in order to allow urging of the pressure vessel in a direction toward or away from pressure seal 620, as illustrated by the double-headed arrow positioned above fixture 610 in FIG. 6A. In various embodiments, fixture 610 may be positioned to the left-hand side (in FIG. 6A) of a length of travel allowed for the fixture, and the pressure vessel placed in position so that the bottom end 607 of the pressure vessel is positioned within or adjacent to the portion of the fixture facing in the right-hand direction. Once the pressure vessel 602 is in position, fixture 610 may be actuated, either manually or using some type actuator device (not shown in FIG. 6A, but for example using a pneumatic or hydraulic cylinder), to urge the pressure vessel to and into sealing contact with the left-hand portion (in FIG. 6A) of pressure seal 620. In various embodiments, additional fixturing 611 may be provided, for example as studs positioned proximate to the pressure vessel, or as a strap or a ring that encircles the pressure vessel at some position along the longitudinal axis of the pressure vessel. The additional fixturing 611 may be configured to guide the movements of the pressure vessel resulting from the actuation of the fixture 610 to align the top opening 612 of the pressure vessel with a sealing face of the pressure seal 620 as fixture 610 urges the pressure vessel into sealing contact with the pressure seal.

In various embodiments, the pressure seal 620 may be a part of the lab vessel. In embodiments, pressure seal 620 may be a separate component. In various embodiments, as an alternative to or in addition to fixture 610, system 600 may include fixture 624. Fixture 624 may be positioned to enclose a portion of the lab vessel 622, including the bottom end of the lab vessel. Fixture 624 may be movable, for example in a direction parallel to a longitudinal axis of lab vessel 622, in order to allow urging of the lab vessel in a direction toward or away from pressure seal 620, as illustrated by the double-headed arrow positioned above fixture 624 in FIG. 6A. In various embodiments, fixture 624 may be positioned to the right-hand side (in FIG. 6A) of a length of travel allowed for the fixture, and the lab vessel placed in position so that the bottom end of the lab vessel is positioned within or adjacent to the portion of the fixture facing in the left-hand direction (in FIG. 6A). Once the lab vessel is in position, fixture 624 may be actuated, either manually or using some type actuator device (not shown in FIG. 6A, but for example using a pneumatic or hydraulic cylinder), to urge the lab vessel to and into sealing contact with the right-hand portion (in FIG. 6A) of pressure seal 620. In various embodiments, additional fixturing 625 may be provided, for example as studs positioned proximate to the lab vessel, or a strap or a ring that encircles the lab vessel at some position along the longitudinal axis of the lab vessel. The additional fixturing 625 may be configured to guide the movements of the lab vessel resulting from the actuation of the fixture 624 to align the top opening 621 of the lab vessel with a sealing face of the pressure seal 620 as fixture 624 urges the lab vessel into sealing contact with the pressure seal.

Once the pressure vessel 602 and the lab vessel 622 have been sealingly coupled as described above, a transfer of one, some, or all of the core samples 604 may be performed to move the core sample(s) from the interior chamber 603 of the pressure vessel into the interior chamber 623 of the lab vessel while maintaining any pressure(s) present in the area within and surrounding the stack the core samples (i.e., the area within interior chamber 603 between end piston 606 and top seal 608). System 600 includes a pressure control system 630 configured to control various pressure levels throughout system 600 in order to accomplish the transfer of the core samples. In various embodiments, pressure control system 630 comprises a pressure source 631 in fluid communication with a plurality of pressure source outputs (636, 638, 640, 642) that are coupled to respective pressure ports (645, 646, 647, 648) through a respective set of individual pressure lines (637, 639, 641, 643). Pressure control system includes a controller 632, which may comprise one or more microcontrollers, and/or a computer system, such as computer system 1000 as illustrated and described below with respect to FIG. 10. As further descried below, controller 632 may be configured to control the application and depressurization of pressure provided at the pressure ports 645, 646,

647, and 648, and thus control operations including transfers of the core samples between the pressure vessel and the lab vessel.

Referring again to FIG. 6A, pressure control system 630 includes a sensor input 633 coupled to one or more sensors, and a user interface 634 communicatively coupled to controller 632. User interface 633 may be configured to be coupled to a plurality of sensor output signal lines, illustratively represented by the dashed lines encircled by ellipse 656, which are coupled to one or more sensors utilized throughout system 600. Examples of sensors may include pressure sensor 651 configured to sense pressure on pressure line 637, pressure sensor 652 configured to sense pressure on pressure line 639 pressure sensor 653 configured to sense pressure on pressure line 641, and pressure sensor 654 configured to sense pressure on pressure line 643. In addition, a sensor array 626 as provided in the lab vessel 622 and comprising an array of sensors is configured to detect the position or one or more pistons/seal located within interior chamber 623 of the lab vessel may be coupled through sensor inputs 633 to controller 632. Additional sensors, such as temperature sensors (not specifically illustrated in FIG. 6A) may also be coupled to provide sensor output signals to controller 632 through sensor inputs 633. User interface 634 is configured to provide a communication coupling between controller 632 and a user interface device 664. The user interface device 664 may be used to monitor and/or provide inputs to control the operations of system 600, including the downloading of programming and/or program control parameters to controller 632. User interface device 664 is not limited to a particular type of device, and may include devices such as a personal computer, laptop computer, smart phone, computer tablet, or other computer devices that may include a display screen or monitor configured to provide graphical output displays, and one or more inputs devices, such as a touchscreen, microphone, computer keyboard, and/or computer mouse, which allows a user to provide input(s) to system 600.

Pressure control system 630 further incudes pressure source 631. Pressure source 631 in some embodiments includes a pressurized vessel that is configured to contain a pressurized fluid, such as an inert gas, that may be used to control movements of core samples and to maintain pressure level(s) within the core samples and within other part of system 600. In various embodiments, pressure source 631 is coupled to an external source of fluid pressure (not shown in FIG. 6A, but for example a pressure tank). In various embodiments, pressure source 631 include control devices, such as valves, fluid conduits coupled to the control valves, and pressure outputs such as pressure sources 636, 638, 640, and 642, which are configured to allow control of pressures applied by pressure control system 630 to the pressure ports 645, 646, 647, and 647, respectively, of system 600 based on outputs control signals provided to pressure source 631 from controller 632. Controller 632 may control the application of pressure to and the depressurization of various portions of system 600 based on pre-programed routines stored within a memory device of the controller, based on user inputs received for example from user interface device 664 through user interface 634, or some combination of pre-programmed routine(s) and user inputs. The operation of system 600 to transfer core samples 604 from pressure vessel 602 to lab vessel 622 is further illustrated and described below with respect to FIG. 6B. As illustrated in FIG. 6A, embodiments of system 600 may include instrumentation 660 configured to perform testing and/or analysis of the core samples and/or gases that may be de-gasses from the core samples once one or more of the core samples have been transferred to the lab vessel 622. The configuration and operation of instrumentation 660 is also further illustrated and described below with respect to FIG. 6B.

In various embodiments, pressure control system 630 is configured to control pressure source 631 in order to perform a transfer of the core samples 604 from pressure vessel 602 into the lab vessel 622. In various embodiments, in order to accomplish the transfer from the pressure vessel into the lab vessel, pressure port 2 (646) may be blocked off, or provided with a pressure equal to the pressure present in the area of the core samples in order to maintain the pressure level present within the stack of core samples. Pressure control system may then be configured to provide an increase in the pressure level provided at pressure port 1 (646), while controllably reducing the pressure provided at pressure port 4 (648). By thereby controlling the pressure differential between pressure port 1 and pressure port 4, a pressure differential is created between the outer face of top seal 608 exposed to a pressure within interior chamber 623 between the top seal and the bottom end 627 of the lab vessel and an outer face of end piston 606 exposed to a pressure present in interior space 609 of the pressure vessel. This pressure differential is regulated to provide enough of a pressure differential to move the stack of core samples, including top seal 608 and end piston 606, in a direction along the longitude axis of the pressure and lab vessels, and transfer the stack of core samples 604 out of the pressure vessel 602, through top opening 612, through passageway 628 of pressure seal 620, and into the interior chamber 623 of the lab vessel 622.

In various embodiments, as the stack of core samples proceeds into the lab vessel, and as the position of top seal 608 passes to the right of pressure port 3 (647), pressure control system 630 may be configured to pressurize pressure port 3 to a pressure needed to maintain the pressure in the area within the stack of core samples, and to close off pressure port 2 (646). Closing off pressure port 2 prevents any pressure from pressure port 2 interfering with the control of the pressure present in the interior chamber 603 of the pressure vessel, and thus the rate and control of the transfer, once end piston 606 has progressed to a position to the right of pressure port 2, while maintaining the ability to regulate the pressure present in the area of the stack of core sample throughout the transfer process. In various embodiments, a distance 644 between pressure port 2 (646) and pressure port 3 (647) is less than a longitudinal length of one core sample. As such, even in instances were a single core sample is being transferred from the pressure vessel to the lab vessel (or from the lab vessel to the pressure vessel), at least one of these two pressure ports will be able to maintain the pressure surrounding the core samples while one or the other of these ports is no longer in fluid communication with the area surrounding the core sample(s) being transferred.

Once the stack of core samples has been successfully repositioned within the interior chamber 623 of the lab vessel, pressure control system 630 may be configured to adjust any pressures provided, and/or to close off pressure port 1 and pressure port 4, so that the stack of core samples remains at a stationary position within the lab vessel. In various embodiments, the setting of any pressures at pressure port 1 and/or pressure port 4 may be adjusted to allow any locking mechanism(s) including as part of top seal 608 and/or end piston 606 to assume a locking position, thus further stabilizing the position of the stack of core samples within the lab vessel.

FIG. 6B illustrates system 600 as illustrated and described above with respect to FIG. 6a, but wherein the core samples 604 have been transferred out of the pressure vessel 602 and positioned within the interior chamber 623 of lab vessel 622. As shown in FIG. 6B, top seal 608 is positioned within interior chamber 623 near the bottom end 627 of the lab vessel, and end piston 606 is positioned within interior chamber 623 and located near top opening 621 of the lab vessel. The core samples 604 are all positioned within the interior chamber 623 of the lab vessel between top seal 608 and end piston 606. In various embodiments, the position of top seal 608 and/or the position of end piston 606 within interior chamber 623 may be detected by one or more sensors included in the senor array 626 that extends along and in parallel to a length of the longitudinal axis of the lab vessel. For example, top seal 608 and/or ed piston 606 may be formed from a magnetic material, or include an insert formed from a magnetic material, which each of the sensors included in sensor array 626 can detect when the seal or piston is positioned adjacent to a particular one of the sensors. By determining which sensor of the senor array is detecting the presence of a seal or piston, the position of the seal or piston with the interior chamber 626 may also be determined. In addition, by knowing the number of core samples and the longitudinal length of each core sample including in stack core samples 604, the location and the position of each of the ends (face of each core sample perpendicular to the longitudinal axis of the interior chamber) of each core sample with the interior chamber 623 may also be determined.

The transfer of the core samples, top seal 608, and end piston 606 may be accomplished by utilizing the pressure controller 630 to manipulate various pressures that are applied to pressure ports 1, 2, 3, and 4, (645, 646, 647, 648, respectively), while maintaining the pressure level present within the core samples in the space between top seal 608 and end piston 606. As shown in FIG. 6B, pressure port 3 (647) is also positioned to be in fluid communication with the space between top seal 608 and end piston 606 that includes the core samples 604. As such, pressure control system 630 may be configured to maintain and/or manipulate the pressure in this space, and thus surrounding the core samples, through pressure source 3 (640) and pressure line 3 (641). For example, pressure control system 630 may proceed to perform a degassing operation of the core samples by allowing pressure surrounding the core samples 604 to be controllably released through pressure port 3. The reduction in the pressure may allow gases present in the core sample(s) to be released, and this released gas or gases may be directed from pressure port 3, through pressure line 3 to the pressure control system 630. The pressure control system may then direct these released gas(es) through test pressure line 662 to instrumentation 660. Instrumentation 660 may include any of the test and/or analysis instrumentation described throughout this disclosure for testing and analysis of the gas(es) being provided from the core samples 604, including but not limited to gas chromatography instruments.

In addition or in the alternative, instrumentation 660 may include one or more types of instruments, such as X-ray, sonic, and/or ultrasonic devices, that may be used to perform tests on and make various measurements of parameters associated with the core samples 604 as they are positioned within the lab vessel as illustrated in FIG. 6B, as illustratively represented by arrow 661. For example, the instrumentation 660 and/or associated downhole and/or surface test equipment may include gamma ray sensors, NMR sensors, acoustic sensors, mechanical sensors, resistivity sensors, other electromagnetic sensors including capacitance sensors or dielectric sensors, optical sensors including spectroscopic sensors such as reflectance sensors or florescence sensors, non-optical spectroscopic sensors imaging sensors including resistivity imaging, acoustic imaging and optical imaging sensors, and chemical sensors such as but not limited to mass spectroscopy sensors, chromatography sensors including gas chromatography sensors or liquid chromatography sensors.

The instrumentation 660 may be conveyed on multiple platforms and used in a plurality of combinations, those platforms being in line, parallel lines, side branch lines or microfluidic. The sensors within instrumentation 660 may be combined within a single inline measurement direction including same point, or angled to measure simultaneously over an overlapping area or volume of the core. The sensors may directly probe the core sample, or a subsample of the core sample including either rock or fluids contained within the core. The measurement area may be small including micro or nano, or macro including the entire core. The measurement may be bulk or surface. The sensors may be used downhole on the coring device or a proximal position therein, or at surface such as in a core transfer device such as a core containment vessel in which core samples are transferred to surface and/or a surface test containment vessel. The sensors may measure rock composition including elemental rock composition, mineral rock composition, rock properties including permeability and porosity, may measure rock mechanical properties or fluid PVT or phase behavior properties. Sensor tests may be performed in replicate at the same or different point, area, or volumetric positions within the core.

The measurements performed by sensors within or associated with the instrumentation 660 may further be used to generate a statistical description of the core including but not limited to an average measurement which may be of higher accuracy than an individual measurement, confidence, or measurement distribution. At least one measurement of at least one type and which may include the statistical description of at least one core, but may also include a plurality of core descriptions, may be used to develop a model of description, refine a model and interpret composition and properties of the at least one core including fluids therein according to a model. The model may be pre-defined. The model may be geologic in nature, physics based in nature or chemistry based in nature. The model as a non-limiting instance may describe the depositional environment, the formation structure including but not limited to fining upwards or fining downward, the distribution or reservoir compartmentalization, the fluids distribution including but not limited to compositional grading, fluid contacts, and reservoir compartmentalization. The measurements, data, statistical description, or results of the model or any combination therein may be used to optimize petroleum prediction, design a completion, or design the production scheme for a field. The production scheme may be related to production rates, production rates over time, equipment needed to produce and or transport the field, or well placement and or well completion. The measurements, data, statistical description or results of a model or any combination therein may be used to decide whether to produce a well or a field.

In various embodiments, the instrumentation 660 may be configured to perform a test on, or make one or more measurements of, the core samples 604 as a whole, without discerning between the individual core samples. In the alternative, instrumentation 660 may include instruments that may be positioned adjacent to a given one or more of individual core samples 604 based on the known position of each core samples within the interior chamber 623. In such embodiments, a particular test or measurements taken may be associated with a single one of the core samples within core samples 604. The instrumentation may then be repositioned so that additional tests, including the same and/or different types of testing and measurements, may be performed that pertain to a different one or more of the core samples included in the stack of core samples 604 now positioned within the lab vessel. In the alternative to moving the instrumentation 660 relative to the position of the core samples 604, the pressure control system 630 may be configured to manipulate the positioning of the core samples 604 within the interior chamber 623, including manipulating the stack of core samples so that some of the core samples may be positioned back within the interior chamber 603 of the pressure vessel, in order to position a particular one of the core samples adjacent to instrumentation 660.

In various embodiments, lab vessel 622 may be composed, at least in part, of a nickel, chromium, cobalt alloy. However, in various embodiments, at least some portion of lab vessel 622, for example a portion of vessel walls proximate to test position indicated by arrow 661, is composed of a material that provides NMR and/or CT transparency to allow for NMR and CT scanning of the core samples that are positioned within the lab vessel. In various embodiments, at least a portion of the lab vessel is composed to provide for NMR and CT transparency. For example, at least a portion of the lab vessel 622 may be composed of Polyetheretherketone (PEEK), fiberglass, etc. In one example, the entire lab vessel is composed of a material to allow for NMR and CT transparency. In another example, one or more windows can be formed in the lab vessel that allows for NMR and CT transparency. In any embodiment of a pressure vessel, lab vessel, or any other device such as a gas valve, fluid conduit, or any other device that potentially comes into contact with the core samples and/or any fluids including gasses that may be expelled form the core samples, the devices may comprise or have interior coatings comprising a material that is inert or at least resistant to any chemical interaction with the core samples and or the fluids/gasses associated with the core samples.

In various embodiments, the interior chamber 623 has a length 649 along longitudinal axis 650 of the lab vessel that allows for positioning of any one of the core samples 604 at a particular position within the interior chamber 623 of the lab vessel, for example as indicated by arrow 655. Length 649 has a length dimension that is long enough to allow all of the core samples, including the left-hand core sample as illustrated in FIG. 6A, to be positioned within the interior chamber 623 adjacent to arrow 655, wherein the pressure in the area of the core samples positioned adjacent to arrow 655 is in fluid communication with pressure port 647, and the testing can be performed on the core samples by instrumentation 660. This positioning can be accommodated while still allowing space at the bottom end 627 of the lab vessel to accommodate an end seal for the stack of core samples and allowing the opening for pressure port 648 to remain to the right of the end seal.

In various embodiments, the testing and analysis of the core samples 604 may be performed prior to the pressure in the area between top seal 608 and end piston 606 is allowed to be depressurized through pressure port 3 (647). In various embodiments, the testing performed by instrumentation 600 related to core samples 604 may be performed at incremental changes in the value of pressure present in the area between top seal 608 and end piston 606 and surrounding the core samples. For example, the pressure in the area of the core samples may be incrementally increased and/or incrementally decreased, and instrumentation 660 operated to perform one or more tests on the core samples, and/or take one or more measurements of parameter(s) associated with the core samples at each of the incremental pressure values.

In various embodiments, the pressure in the area of the core samples, may be increased to a level that is the same as or a higher level than the original pressure present in the pressure vessel 602 when the pressure vessel and core sample were originally delivered to the surface by a coring tool after initial collection of the core samples. One or more tests or measurements may be performed/taken using instrumentation 660 at these higher pressure levels.

In various embodiments, pressure control system may be configured to transfer core samples 604 back into the pressure vessel, to a position as illustrated in FIG. 6A, wherein least some number or all of the core samples have been transferred into the interior chamber 623 of the lab vessel 622, for example as illustrated in FIG. 6B. In various embodiments, in order to accomplish the transfer from the lab vessel back into the pressure vessel, pressure port 3 (647) may be blocked off, or provided with a pressure equal to the pressure present in the area of the core samples in order to maintain the pressure level present within the stack of core samples. Pressure control system may then be configured to provide an increase in the pressure level provided at pressure port 4 (648), while controllably reducing the pressure provided at pressure port 1 (645). By thereby controlling the pressure differential between pressure port 1 and pressure port 4, a pressure differential is created between the outer face of top seal 608 exposed to a pressure within interior chamber 623 between the top seal and the bottom end 627 of the lab vessel and an outer face of end piston 606 exposed to a pressure present in interior space 603 of the pressure vessel. This pressure differential is regulated to provide enough of a pressure differential to move the stack of core samples, including top seal 608 and end piston 606, in a direction along the longitude axis of the pressure and lab vessels, and transfer the stack of core samples 604 back into the interior chamber 603 of the pressure vessel.

In various embodiments, as the stack of core samples proceeds into the pressure vessel and the position of end piston 606 passes to the left of pressure port 2 (646), pressure control system 630 may be configured to pressurize pressure port 2 to a pressure needed to maintain the pressure in the area within the stack of core samples, and to close off pressure port 3 (647). Closing off pressure port 3 prevents any pressure from pressure port 3 interfering with the control of the pressure present in the interior chamber 623, and thus the rate and control of the transfer, once top seal 608 has progressed to a position to the left of pressure port 3, while maintaining the ability to regulate the pressure present in the area of the stack of core sample throughout the transfer process.

In various embodiments and a related to the transfer of core samples both from the pressure vessel to the lab vessel and from the lab vessel back into the pressure vessel, the longitudinal axes of the pressure vessel and that lab vessel may be tilted to a non-perpendicular angle relative to gravity so that the weight of the core samples themselves may aid in the movement of the core samples from one vessel to the other vessel. In various embodiments, the pressure vessel/lab vessel combination may be positioned on a rotatable fixture so that the angle of the longitudinal axes of the pressure vessel and the lab vessel may be adjusted to that the vessel into which the core sample(s) are to be transferred into is lower, relative to gravity, than the vessel where the core sample(s) are being transferred from. This relative positioning, in conjunction with the control of various pressures within the system, may contribute the ease of moving the core sample(s), and thus completing the transfer.

Once the stack of core samples has been successfully repositioned within the interior chamber 603 of the pressure vessel, pressure control system 630 may be configured to adjust any pressures provided, and/or to close off pressure port 1 and pressure port 4, so that the stack of core samples remains at a stationary position within the pressure vessel. In various embodiments, the setting of any pressures at pressure port 1 and/or pressure port 4 may be adjusted to allow any locking mechanism(s) including as part of top seal 608 and/or end piston 606 to assume a locking position, thus further stabilizing the position of the stack of core samples within the pressure vessel.

In various embodiments, after transferring the stack of core samples back into the pressure vessel, top seal 608 is configured to again provide a pressure seal, locking in the pressure level present in the area of the core samples. Pressure port 2 (646) may remain in fluid communication with the area pressurized and surrounding the core samples, and may be closed off or pressurized, by pressure provided by pressure source 631, to maintain a desired level of pressure within the area of the core samples. In various embodiments, once the transfer has been completed, pressure control system 630 may be configured to depressurize the interior chamber 623 of the lab vessel, and thus allow for decoupling and removal of the lab vessel from pressure seal 620 and the pressure vessel. The positioning of top seal 608 prevents any depressurization of the area where the stack of core samples is located despite the removal of the lab vessel. One reasons for removal of the lab vessel is to replace the lab vessel with a different lab vessel. Such as a lab vessel comprise of a different material that would allow one or more different types of testing to be performed on the core samples when transferred back into the replacement lab vessel that would not be able to be performed when the core stack was present in the original lab vessel. Another reason for removal of the lab vessel may be to replace the original lab vessel with a lab vessel that includes one or more different devices or apparatus, such as a singular, that allow the performance of one or more operations that would not be available using the original lab vessel. Various tests and analysis agendas that may be performed on the stack of core samples may require the use of a plurality of different lab vessels, each lab vessel required at a particular stage of the testing and analysis, and therefore the ability to change out the lab vessels while maintaining and/or manipulating the pressure within various portions of system 600 provides a high level of flexibility and range with regards to the testing that may be performed on a particular set of core samples.

Transferring the core samples to the lab vessel while maintaining the pressure(s) surrounding the core samples provide for a wide variety of types and formats for testing and analysis related to the core samples. For example, canister gas desorption experiments are routinely applied within shale gas reservoirs for the determination of volumetric hydrocarbon gas in place estimates. Conventional approaches required extensive operator intervention and typically used a rudimentary volumetric measurement recording apparatus. Example embodiments include a computer-controlled and automatic data recording canister gas desorption to eliminate multiple limitations of conventional approaches. For example, with the application of example embodiments, limitations of automatic pressure maintenance, continuous data recording, and fluid solubility manometer effects are removed from monitoring of gas desorption.

Embodiments of system 600 may include an Archimedes bulk volume measurement system that can rapidly and accurately determine the bulk volume (VBbulk) of a saturated or partially saturated sample gravimetrically. The bulk volume can be determined by weighing a sample suspended in the air and weighing the sample submerged under liquid. The weight difference can then be divided by the liquid density to provide the bulk volume of the sample. Conventional approaches use water as the liquid. However, water can create significant problematic results when used as an immersion fluid for core samples from a subsurface formation as described herein. For example, water can interact with rock clay minerals and miscibility with connate waters present with rock porosity of the core samples. Instead of using water to measure the liquid density, some embodiments use a nonwetting and nonmiscible liquid (such as a fluorinert liquid). Such embodiments can eliminate both rock and rock pore fluid.

Archimedes bulk volume measurements may be performed on core sample(s) that are no longer being maintained at the pressure level(s) that were present downhole when and where the core samples were originally collected, and therefore may be performed in a vessel other than the pressure vessel and/or the lab vessel as described throughout this disclosure. In various embodiments, Archimedes bulk volume measurements comprise measuring the volume of the core samples as the difference between the core vault and the residual volume of fluid in the core vault. In various embodiments, the core samples are contained in or surrounded by an exclusion or buffer fluid. In embodiments where the buffer fluid has a unique signature, its volume may be measurable by an external sensor. The weight of that fluid and the weight of the container can be subtracted from the weight of the container+fluid+core to yield the weight of the core. Using the volume of the core and the weight of the core, the density of the core may be calculated in place.

An example operation as part of performing analysis of the core sample can include volumetric gas depletion. Conventional approaches included an uncontrolled release of gas from the pressurized vessel. Some embodiments include a computer-controlled constant gas rate volumetric depletion/expansion while recording of pressure and temperature data of the produced gas. For example, the pressure and temperature data of the produced gas can be high-resolution. Thus, gas can be released from the pressurized vessel at a constant rate to determine how the pressure changes.

Improved reservoir modeling and determination of principle reservoir properties can result from such analysis of the core samples extracted using the coring tool as described herein. For example, such operations can determine absorbed content versus free gas content of the core sample. A production profile of the formation changes as a function of the ratio of the absorbed content to free gas content.

FIGS. 6C-6F illustrate a system 690 according to various embodiments. System 690 includes a pressure vessel 602 coupled to a lab vessel 622 and a pressure control system 630. System 690 may include the same or similar devices, arranged and configured to provide all of the features and/or all of the functions as illustrated and described above with respect to system 600 and FIGS. 6A-6B, but with the additional features and functions as described below. For the sake of clarity, some of the details illustrated and described with respect to system 600 and FIGS. 6A-6B are omitted from one or more of FIGS. 6C-6F, but may be included in various embodiments to system 690.

Figure 6C:
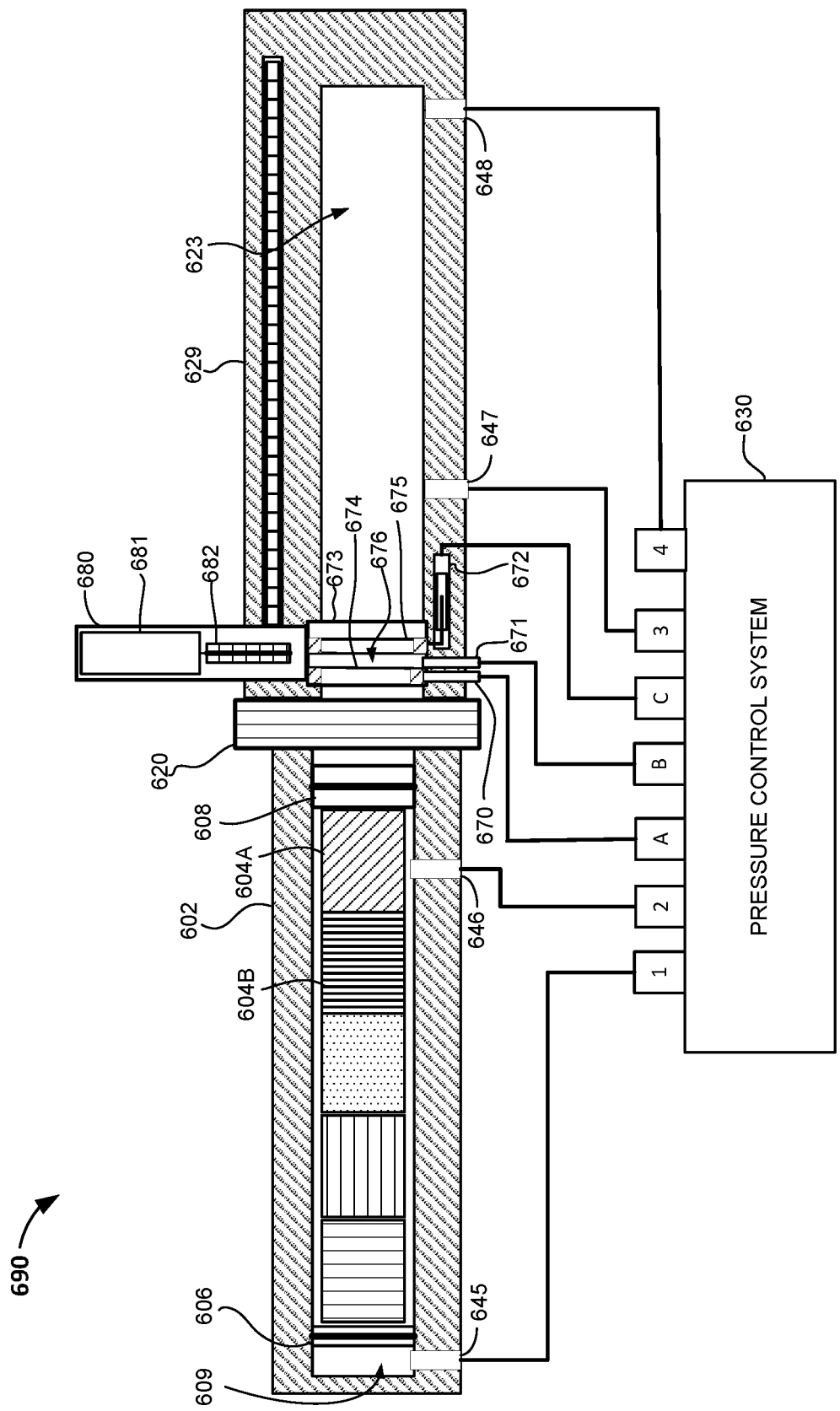
FIGS. 6C-6F illustrate core sample simulation procedures according to various embodiments.

As illustrated in FIG. 6C, system 690 includes a pressure vessel 602 configured to have a stack of core samples positioned within an inner chamber of the pressure vessel. A lab vessel 629 is sealingly coupled to the pressure vessel 602 by pressure seal 620, and configured to allow the transfer of core samples included in the stack of core samples back and forth between the pressure vessel and the lab vessel. A different between lab vessel 629 and embodiments of lab vessel 622 described above (FIGS. 6A-6B) is the inclusion of a singulator 673 positioned near the top opening of the lab vessel in lab vessel 629. Singulator 673 may be configured to be controlled by the pressure control system 630 to separate and provide a single core sample, or some number of core samples less than the total number of core samples remaining in the stack core samples, to the inner chamber of lab vessel 629. Once singulated for the stack of core samples, the individual core sample(s) may be positioned within the lab vessel, and the pressure in the area of the singulated core sample(s) may be manipulated separately from any pressure(s) being maintained in the area(s) of the remaining core samples, thus allowing testing and analysis of only the singulated core sample(s).

As shown in FIG. 6C, singulator 673 includes an outer collar 674, and inner collar 675, and a space 676 separating the outer collar from the inner collar. Each of the outer collar and the inner collar may comprise a ring shape apparatus that encircles a portion of the longitudinal axis of lab vessel 629, the ring shapes having interior shape and interior dimensions configured to allow passage of the core samples through the ring shape. In various embodiments, at least one or both of the outer collar and the inner collar are configured to be articulated for movement in a direction parallel to the longitudinal axis of lab vessel 629. For example, as illustrated in FIG. 6C the inner collar 675 is coupled to a actuator 672. Actuator 672 may be configured to move the inner collar 675 between a first position closest to outer collar 674 and a second position farther away from outer collar 674, the movements in various embodiments based on pressure inputs provided through a pressure line coupled to the pressure control system 630.

In addition, each of the outer collar 674 and the inner collar 675 may comprise a gripper mechanism, such as an inflatable sleeve or mechanical grippers, that may be actuated to allow the respective collar to grip a portion of a core sample that is located within the inner ring shape of the respective collar. For example, outer collar 674 may include an inflatable sleeve or a set of mechanical grippers that may be actuated to grip a core sample, and de-actuated to release the grip on a core sample, based on control of a pressure proved to outer collar 674 by the pressure control system 630 through pressure port A (670). Similarly, inner collar 675 may include an inflatable sleeve or a set of mechanical grippers that may be actuated to grip a core sample, and de-actuated to release the grip on a core sample, based on control of a pressure proved to inner collar 675 by the pressure control system 630 through actuator 672, or a separate pressure port coupled to the inner collar. In order to utilize these gripping features as provided by the singulator, a stack of core samples may be positioned so a seam between two individual core samples is positioned within the singulator 673, and so that the seam is located and aligns with the space 676 between the outer collar and the inner collar, and a portion of a first one of the core samples aligns with the outer collar and a portion of the second one of the core samples aligns with the inner collar.

Figure 6D:
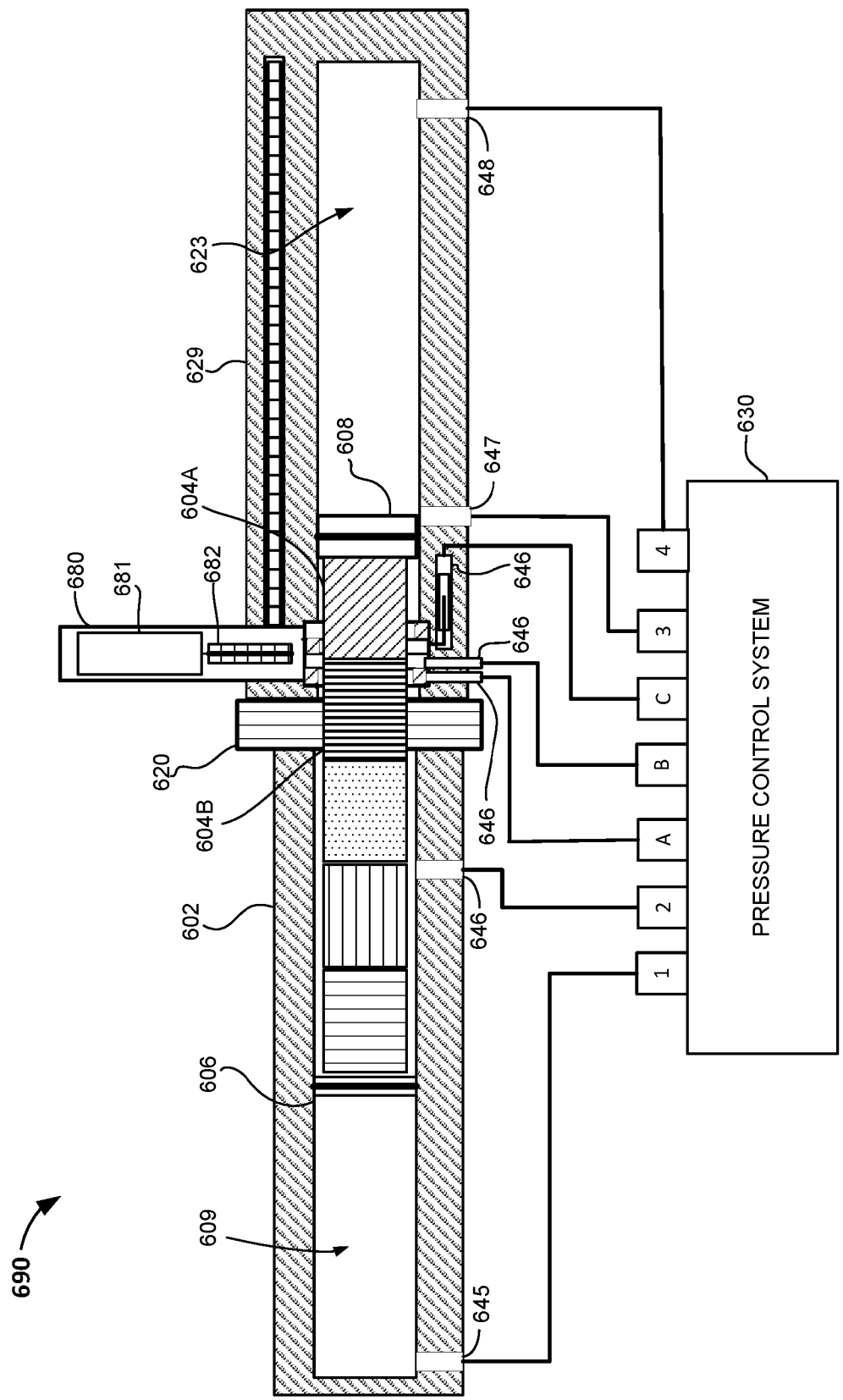

FIG. 6D illustrates system 690 having a first core sample 604A positioned so that a portion of the core sample 604A is positioned within the ring shape of inner collar 675, a portion of the second core sample 604B is positioned with the ring shape of the outer collar 674, and the seam between the core sample 604A and 604B is positioned with space 676. Once positioned as such, the pressure control system may be configured to actuate each of the gripper mechanism(s) of the outer collar and the inner collar, thus securing the positions of the first and second core samples. Once secured by the inner and outer collars, pressure control system 630 may be configured to actuate actuator 672 to cause the inner collar 675 to move to the second position that is farthest away from the outer collar 674, thus creating a space between the end of the first one of the core samples relative to the proximate end of the second one of the core samples.

Figure 6E:
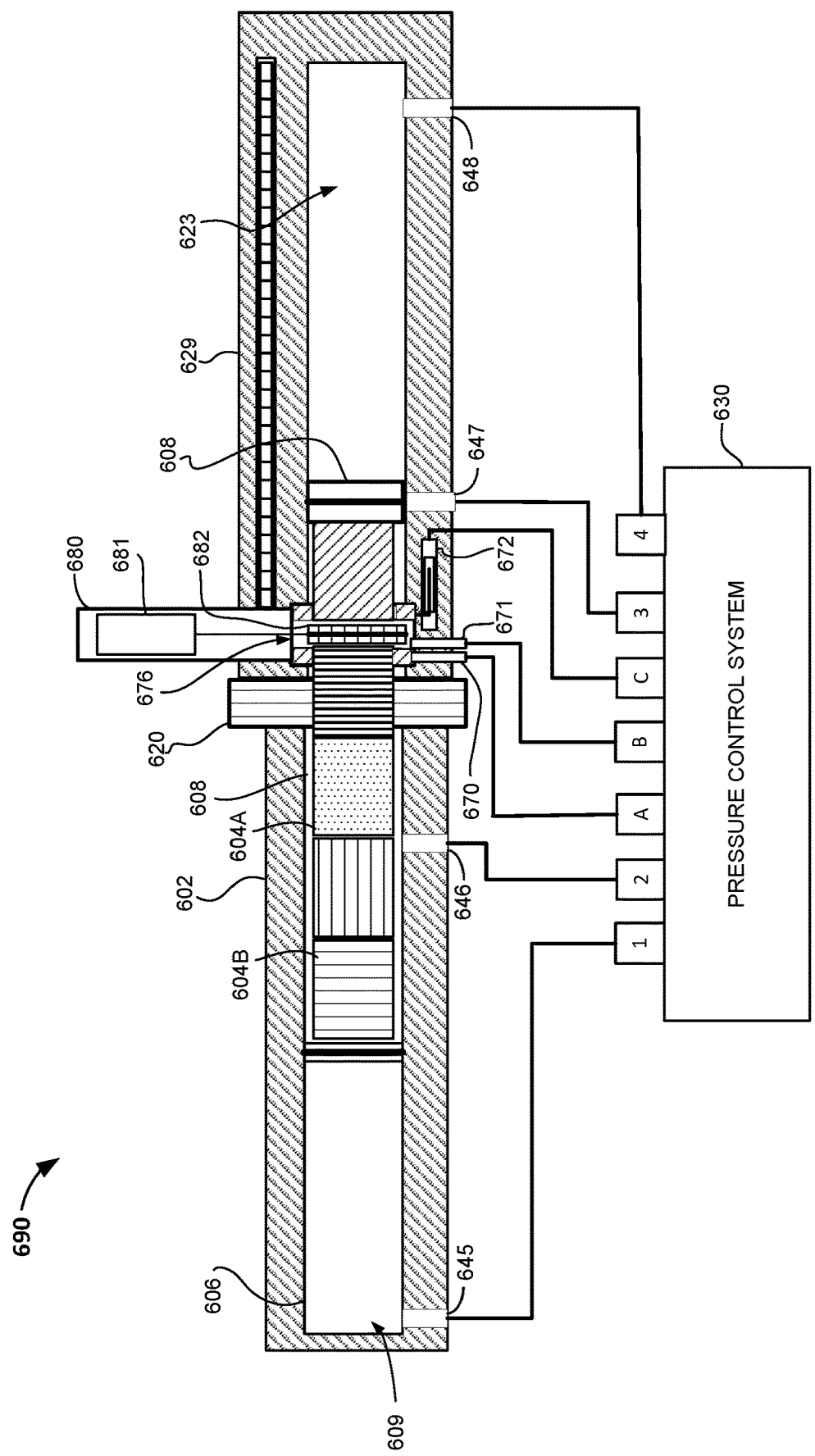

FIG. 6E illustrates system 690 after having secured the first core sample 604A and the second core sample 604B with the inner and outer collars, respectively, and then having actuated actuator 672 to move first core sample 604A away from the second core sample 604B in order to create a space between the adjacent end surfaces these core samples. In various embodiments, system 690 includes a seal inserter unit 680 comprises an actuator 681 configured to insert a seal, such as seal 682, into the space created by the singulator between the adjacent ends for the first and second core samples. FIGS. 1C and 1D illustrate the seal inserter unit 680 with a seal 682 loaded into position for insertion, while FIG. 1E illustrates the seal 682 having been inserted into space 676 following the separation of the first and second core samples from one another.

With at least one seal in place between the separated core samples 604A and 604B, and by releasing the gripping mechanism for example on only the inner collar 675 to release the grip on the first core sample 604A while maintaining the grip provided by the outer collar on the second core sample 604B, pressure may be applied by pressure control system 630 to pressure port B (671). The application of pressure at pressure port B may be configured to increase the pressure on the inserted seal 682, and the first core sample 604A, and in further conjunction with control of the pressure within the inner chamber 623 via pressure port 4 (648), move the now separated first core sample 604A away from and out to the singulator and further into the lab vessel 629. In various embodiments, after moving the first core sample 604A away for the singulator, seal insertion unit 680 may be configured to insert another seal into space 676. This additional seal, in conjunction with de-actuation of the outer collar 674 to release the grip on the second core sample 604B, and the pressure control system 630 controlling the pressures applied to pressure port B (671) and pressure port 1 (645), may be used to transfer the remaining core samples including core sample 604B that were separated from the core sample 604A now positioned within the lab vessel back into the pressure vessel, and including a seal (second seal provided by the seal insertion unit 680), to maintain an separate pressure level with the stack of core samples now separated from the first core sample.

Figure 6F:
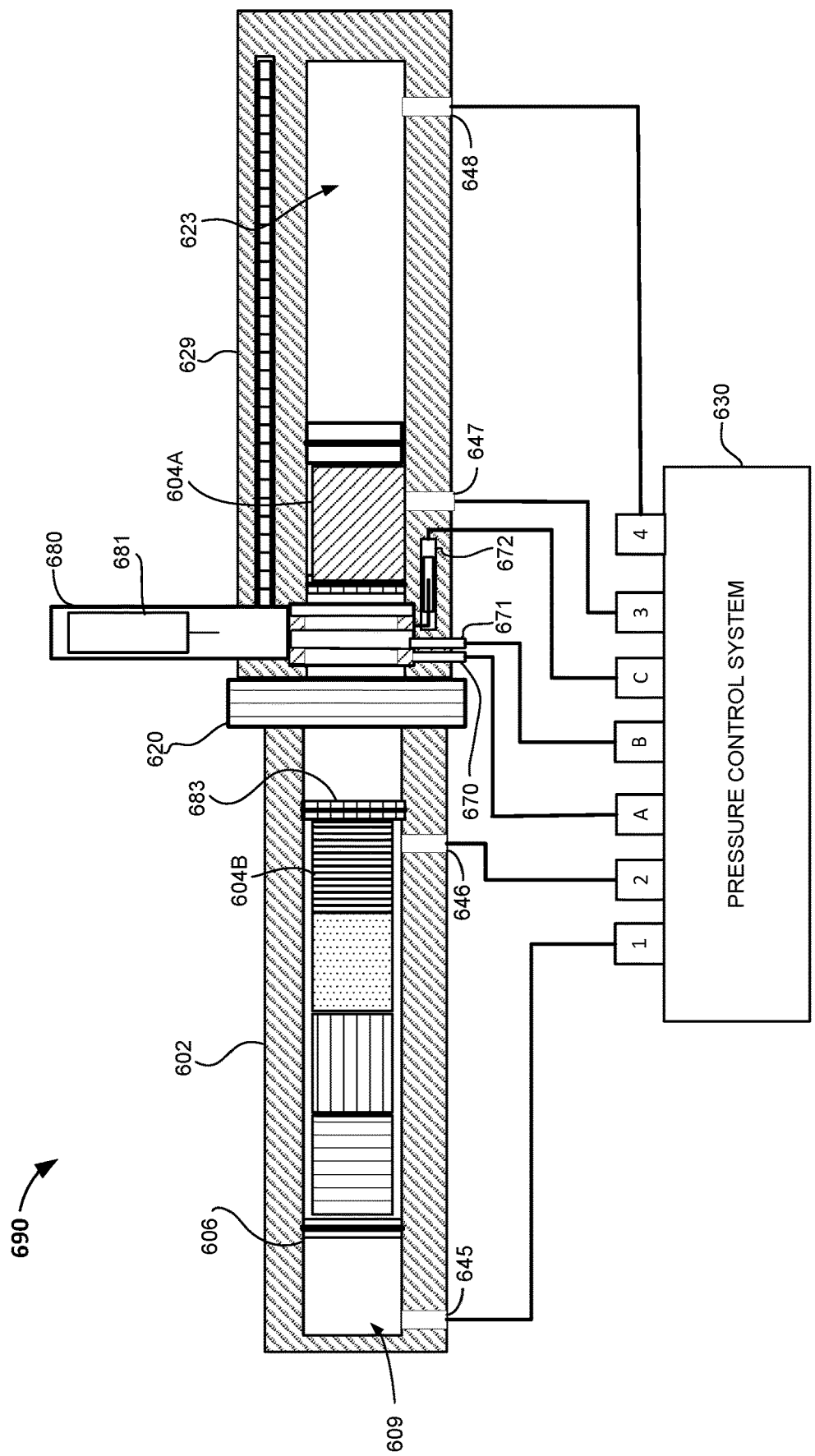

FIG. 6F illustrates system 690 having singulated first core sample 604A from the second core sample 604B, and having transferred the first core sample 604A out of singulator 680 and into the interior chamber 623 of the lab vessel 629, while also moving the remaining stack of core samples, including second core sample 604B, out and away from the singulator and back into the interior chamber of the pressure vessel

602. As also illustrated in FIG. 6F, the singulated core sample 604A is sealed on both ends by top seal 608 and inserted seal 682, and is positioned over pressure port 3 647) so that the pressure control system 630 may thereby control the pressure surrounding first core sample 604A, including performing pressurizations and depressurizations of the first core sample 604 without having an effect on the pressure present in the area souring the remaining core samples, including second core sample 604B. Further, the remaining stack core samples, including second core sample 60B, is sealed on both ends by end piston 606 and the second inserted seal 683, and is positioned over pressure port 2 (646). As such, pressure control system 630 may be configured to maintain and/or manipulate the pressure present in the area surrounding the remaining stack of core samples independently of any pressure changes occurring with respect to the simulated first core sample 604A.

The ability to separate one or more core samples for the remaining core samples included in a stack of core samples allow for the individual testing, for example gas extraction testing, of the singulated core sample(s) without the need to incur any changes, for example pressure changes, the might affect the status or condition of the remaining core samples. This singulation process may be repeated, for example by testing and then removing the testes core sample(s) from lab vessel 629, for example through a bottom seal in the lab vessel, and then performing another singulation operation as described above to position a next or another core samples or set of core samples within the lab vessel 629. In various embodiments, each of the individual core samples present in a pressure vessel, such as pressure vessel 602, couple be simulated from the remaining core sample (in the stack of core samples, and individually tested and analyzed after positioning of the simulated core sample(s) within the lab vessel while separately maintaining the condition of and pressure surrounding the remaining core sample(s).

Figure 6G:
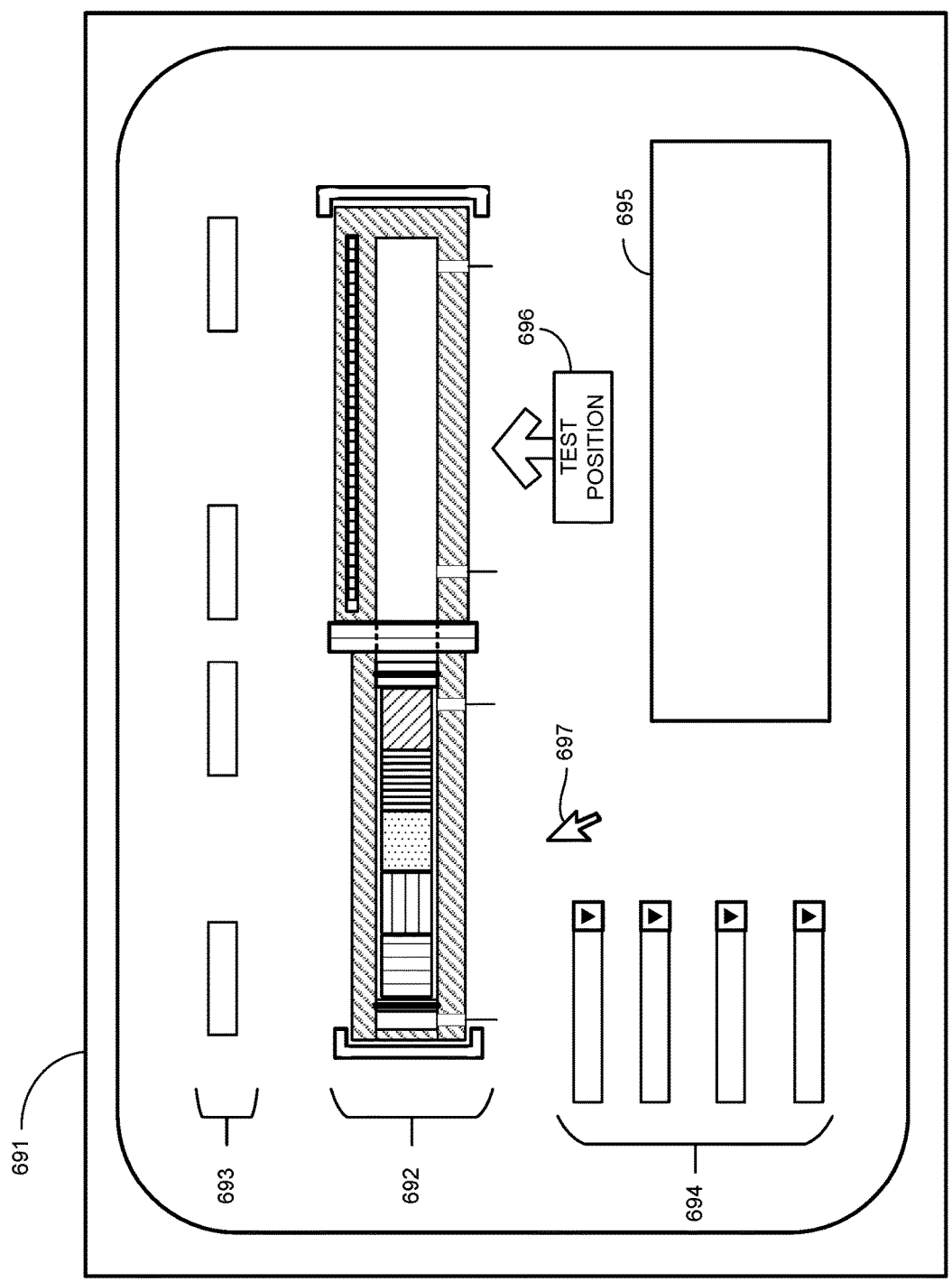
FIG. 6G illustrates a graphical user interface according to various embodiments.

FIG. 6G illustrates a graphical user interface (GUI) 691 that may be utilized in in a core sample test system according to various embodiments. In various embodiments, GUI 691 may be incorporated with as part of a user interface, such as user interface 664 (FIGS. 6A-6B), which allow a user, such as an engineer or a test technician, to interact with a core sampling test system, such as system 600 or system 690 described above. GUI 691 may be display various types of graphical information, including text and other graphical representations, on a display screen as illustrated in FIG. 6G. The display may be a touch screen, which allows for user inputs and other interactions to be made to a system, such as test system 600 or system 690, through touches and gestures made to the display. In various embodiments, a user may also or in the alternative interact with GUI 691 through manipulation of cursor 697, which for example may be controlled by a user though a device such as a computer mouse.

In various embodiments, GUI 691 may include one, some combination of, or all of the following features. GUI 691 may include a graphical depiction, indicated by bracket 692, which represents the arrangements and/or a current status of a core sampling test system. For example, the graphical depiction may include a graphical representation of a pressure vessel coupled to a lab vessel. The current position and arrangement of core samples with the pressure vessel and/or the lab vessel may also be represented in the graphical depiction. The position of the core samples may be updated in real time to show movements of the core samples, for example as the core samples are transferred from the pressure vessel to the lab vessel or visa-versa, and to illustrate the actual positions of the core sample( ) for example relative to a test position, such as test position 696, or relative to a singulator station (not shown in FIG. 6G, but see FIGS. 6C-6H), which may be included in the test system being depicted on the GUI.

Additional information and other types of graphical depictions related to a core sample test system may be included as part of the display being provided by GUI 691. For example, a plurality of text boxes, indicated by bracket 693, may be displayed, wherein the text boxes may be configured to display a value for pressure level at a particular area within the test system, for example being provided at an pressure port in fluid communication with an area inside the pressure vessel or the lab vessel. In various embodiments, a one or more pull-down menus, indicated by bracket 694, may be provided that allow a user to select various features, and initiate various operations to be performed by the test system, by selection of an option provided as part of a pull-down menu. For example, a user may select an option from a pull-down menu to initial a transfer to the core samples from the pressure vessel to the lab vessel or visa-versa, or for example to control positioning of a particular one of the of the core samples to align the particular core sample with the test position 696. In various embodiments, one or more types of test procedures may be initiated by a user based on a selection from one or more of the pull-down menus.

A test box 695 may be included in various embodiments of GUI 691. Text box 695 may be used to display information, such as test results, system warning messages, and any other type of information related to the test system associated with the display. In various embodiments, text box 695 is configured to allow a user to input information, (for example using a computer keyboard), such as text and/or numerical values, that may be utilized to control the test system, such as operating parameters for controlling the operation of the test system, and/or to otherwise manipulate data, such as issue a save function, for data generated by the core sample testing. Other possibilities for the display and types of interactions that may be utilized to monitor and to operate a core sample test system are possible and are contemplated for use as part of GUI 691.

Figure 7:
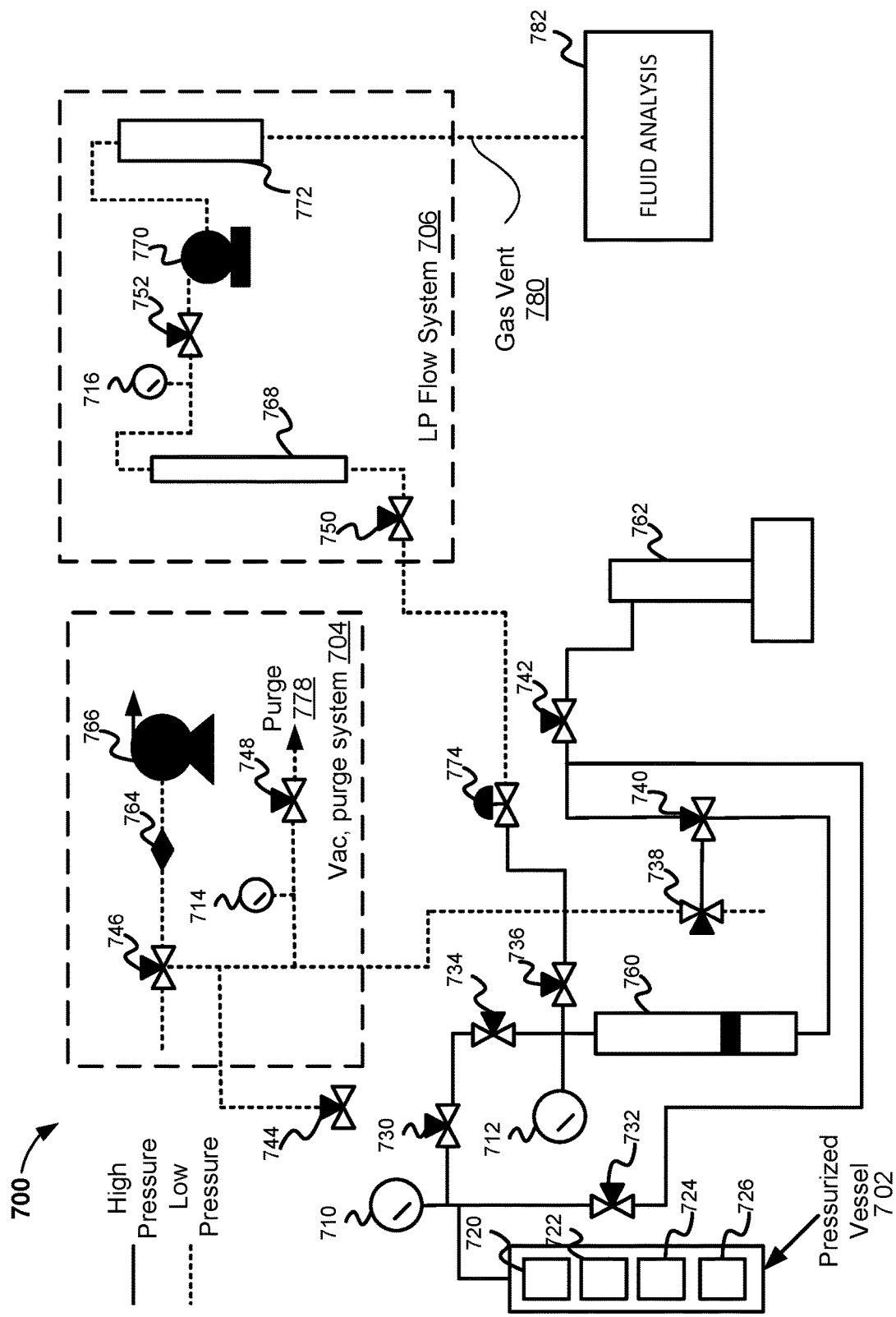
FIG. 7 illustrates an example system for performing analysis of a core sample that includes a computer-controlled constant gas rate volumetric depletion, according to some embodiments.

FIG. 7 depicts an example system for performing analysis of a core sample that includes a computer-controlled constant gas rate volumetric depletion, according to some embodiments. FIG. 7 depicts a pressure control and gas desorption system 700 that includes measure gauges 710, 712, 714, and 716 and valves 730, 732, 734, 736, 738, 740, 742, 746, 748, 750, and 752. The system 700 also includes a filter 764, a vacuum pump 766, a floating piston accumulator 760, a syringe pump 762, a gas flow filter 768, a gas meter 770, a gas sampler 772, and a pressure regulator 774.

The system 700 includes a vacuum purge system 704 and a low pressure gas flow system 706. The vacuum purge system 704 includes the valve 746, the filter 764, the vacuum pump 766, a measure gauge 714, and a valve 748. The low pressure gas flow system 706 includes the valve 750, the gas flow filter 768, the measure gauge 716, the valve 752, the gas meter 770, and the gas sampler 772. Connections among the components of the system 700 include high pressure flow connections (depicted as solid lines) and low pressure connections (depicted as dashed lines).

A pressurized vessel 702 of a coring tool includes core samples 720, 722, 724, and 726. A valve or outlet of the pressurized vessel 702 is connected (high pressure) to the measure gauge 710, a first port of the valve 730, and a first port of the valve 732. A second port of the valve 730 is connected (high pressure) to a first port of the valve 734. A second port of the valve 734 is connected (high pressure) to a measure gauge 712, a first port of the valve 736 and a first port of the floating piston accumulator 760. A second port of the valve 736 is connected (high pressure) to a first port of the pressure regulator 774. A second port of the pressure regulator 774 is connected (low pressure) to a first port of the valve 750.

A second port of the valve 732 is connected (high pressure) to a first port of the valve 740 and a first port of the valve 742. A second port of the floating piston accumulator 760 is connected (high pressure) to a second port of the valve 740. A port of the syringe pump 762 is connected (high pressure) to a second port of the valve 742.

A first port of the valve 738 is connected (low pressure) to output the gas. This serves as a purge line used in initial system setup prior to processing the core samples from the coring tool. A second port of the valve 738 is connected (high pressure) to a third port of the valve 740. A third port of the valve 738 is connected (low pressure) to a first port of the valve 746, a port of the valve 744, a measure gauge 714, and a first port of the valve 748. A second port of the valve 746 is connected (low pressure) to a gas/fluid system purge line used in initial system setup prior to processing the core samples from the coring tool. A third port of the valve 746 is connected (low pressure) to a first port of the filter 764. A second port of the filter 764 is connected (low pressure) to a first port of the vacuum pump 766. A second port of the vacuum pump 766 is connected to output vacuum pump exhaust to ambient air. A second port of the valve 748 is to output (low pressure) a purge 778 of the gas.

A second port of the valve 750 is connected (low pressure) to a first port of the gas flow filter 768. A second port of the gas flow filter 768 is connected (low pressure) to a measure gauge 716 and a first port of the valve 752. A second port of the valve 752 is connected (low pressure) to a first port of the gas meter 770. A second port of the gas meter 770 is connected (low pressure) to a first port of the gas sampler 772. A second port of the gas sampler 772 is connected (low pressure) as an output of gas (gas vent 780). Prior to processing the core samples from the coring tool, the system can be cleared of any prior containment using an inert gas (such as helium, argon, nitrogen, etc.) through the use of the valves. System 700 further includes a fluid analysis system 782 that receives the desorbed gas from low pressure gas flow system 706 such as via gas vent 780. As depicted and described with reference to FIGS. 2 and 8, fluid analysis system is configured to include gas composition testing components and saturation point testing components for analyzing fluids desorbed from the core samples.

Figure 8:
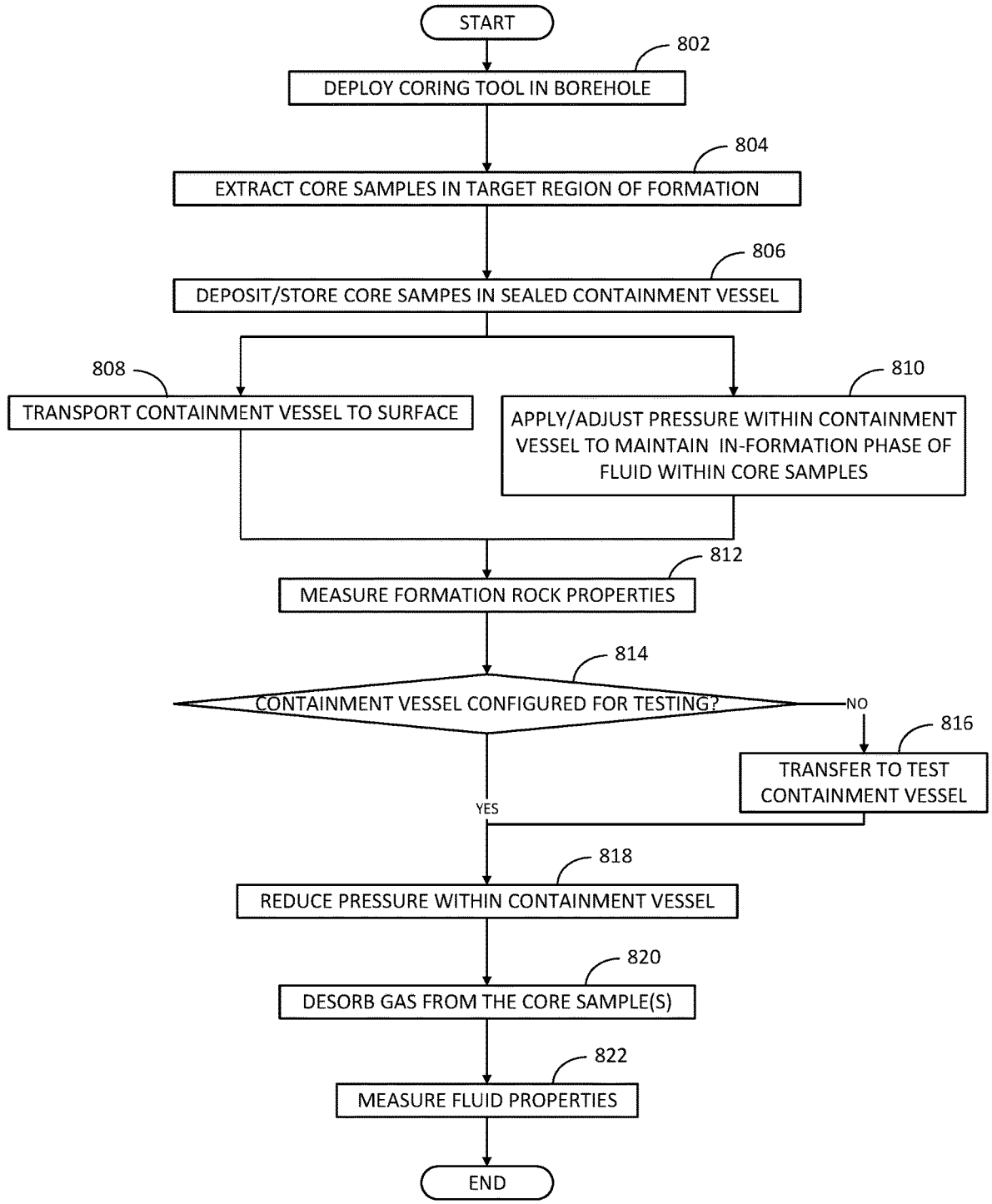
FIG. 8 is a flow diagram depicting operations and functions for testing and otherwise processing core samples in accordance with some embodiments.

FIG. 8 is a flow diagram depicting operations and functions for testing and otherwise processing core samples in accordance with some embodiments. The operations and functions depicted and described with reference to FIG. 8 may be performed by any of the system, devices, and components depicted and described with reference to FIGS. 1-7. The process begins as shown at block 802 with a coring tool being deployed within a borehole such as part of a LWD drilling rig or a wireline apparatus. During a core sample collection process, for instance, the coring tool may be deployed at one or more downhole zones that have been selected for testing formation material and fluid properties.

At block 804, the coring tool is used to extract one or more core samples in a selected region/depth of the borehole. The coring tool is configured to include cutting and "catching" means as previously disclosed and is further configured to include a receptacle section including a containment vessel into which the one or more core samples are deposited after being removed from the formation. At block 806, the core samples are deposited and stored within the containment vessel that includes a sealed interior core chamber in which the cores are stored. As part of the storage processing, the coring tool may initially pressurize the containment vessel to a pressure approximately the same as or offset by a specified threshold from a measured downhole hydrostatic pressure.

Following or between core sample collection cycles, the drilling rig or wireline apparatus transports the containment vessel to the surface (block 808). During transport, one or more phase related fluid properties such as pressure and temperature may be adjusted to maintain the in-formation phase (e.g., liquid, gas, and/or mixed for different fluid components) of fluids within the core samples (block 810). Following transport, the containment vessel may be removed from the coring tool to enable testing the lithology (e.g., material and structural characteristics such as porosity and permeability) and fluid properties of the core samples. As shown at block 812, testing may begin with measurement of the lithological properties such as porosity and permeability of the core samples within the containment vessel. In some embodiments, the containment vessel may be configured using testing compatible materials to implement NMR and/or CT scan testing of the cores. The containment vessel in which the lithology measurements are performed may be the transport containment vessel.

As shown at blocks 814 and 816, the core samples may be transported to a test containment vessel for fluid testing and additional formation rock testing. Components and procedures for transferring the core samples are depicted and described with reference to FIGS. 6A-6F. To implement fluid testing, the core samples are brought to an equilibrium state at least in terms of pressure and temperature. The fluid within the core samples remains contained within the core sample rock (for tight formation material) and/or in substantially the same phase condition as when extracted by the coring tool.

As shown at block 818, a pressure control and gas desorption system reduces pressure within the containment vessel and may concurrently or subsequently desorb gas from the containment vessel (block 820). During and following the period of pressure reduction and partially or fully overlapping gas desorption process, the system, may be configured to measure properties of the fluids contained in the core samples (block 822). For instance, the system may be configured to determine a saturation point in terms of pressure and temperature of the core sample fluids such as a bubble point for oil formation core samples and dew point for retrograde condensate formation core samples. Furthermore, the system may be configured to measure the compressibility of the core samples within the containment vessel and may determine the saturation point based, in part, on the measured compressibility. In some embodiments, instrumentation such as instrumentation 660 may be configured to measure concentrations of one or more gas components of the desorbed gas at multiple points during desorption of gas from the core sample. The instrumentation may be further configured to determine an integral amount of the gas component at one or more of the multiple points based on the measured gas component concentrations.

The system may be further configured to detect and measure specified chemical components within the desorbed gas. For example, the system may include a gas chromatograph that receives the desorbed gas and measures various gaseous chemical components and compounds such as carbon dioxide and sulfur hydroxide. The system may be concurrently reducing pressure and recording the chemical component levels (e.g., concentrations, volumes) in association with temporally corresponding pressures and temperatures. In some embodiments, the system may be configured to detect one or more of a variety of gases of interest including hydrogen sulfide, carbon dioxide, and mercury. In some embodiments, the system may be configured to measure concentrations of one or more gas components of the desorbed gas at multiple points during a de-pressure, and desorption cycle. In this manner, the system may calculate or otherwise determine an integral amount of the gas component(s) at one or more of the multiple concentration measurement points based on the measurements. In some embodiments, the system may be configured to determine a rate of desorption of a particular gas component (e.g., hydrogen sulfide) over a range of phase related fluid property values such as pressure and/or temperature range.

Figure 9:
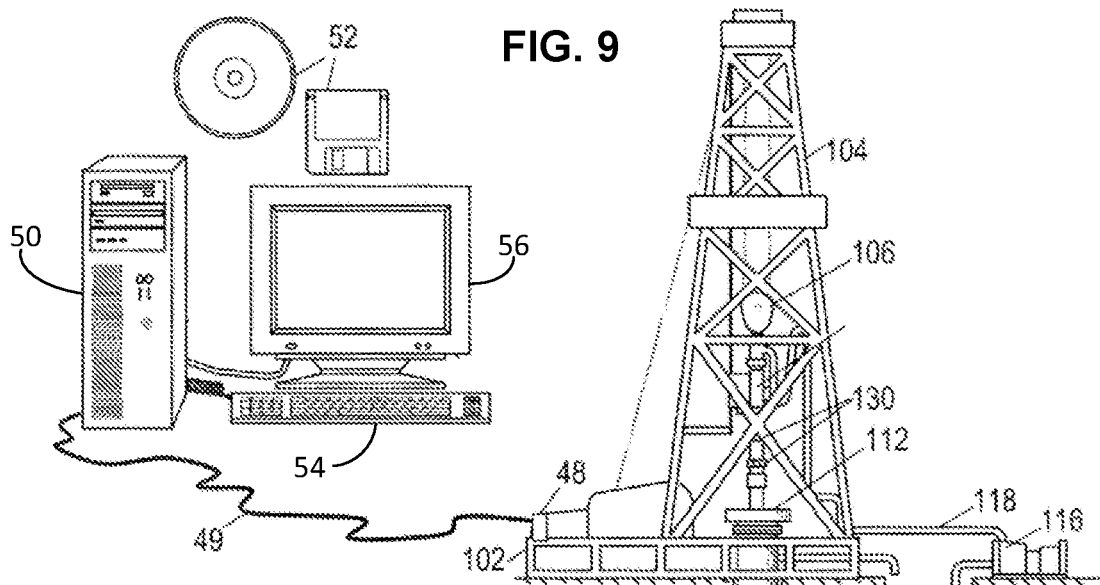
FIG. 9 illustrates an example coring while drilling environment, according to some embodiments.

FIG. 9 depicts an example coring while drilling environment, according to some embodiments. In the illustrated context, a drilling platform 902 is equipped with a derrick 904 that supports a hoist 906 for raising and lowering a drill string 908. The hoist 906 suspends a top drive 910 that rotates the drill string 908 as the drill string is lowered through the well head 912. The drill string 908 can be extended by temporarily anchoring the drill string at the well head 912 and using the hoist 906 to position and attach new drill pipe sections with threaded connectors 907.

Connected to the lower end of the drill string 908 is a drill bit 914. As bit 914 rotates, it creates a borehole 920 that passes through various formations 921. A pump 916 circulates drilling fluid through a supply pipe 918 to top drive 910, through the interior of drill string 908, through orifices in drill bit 914, back to the surface via the annulus around drill string 908, and into a retention pit 924. The drilling fluid transports cuttings from the borehole into the pit 924 and aids in maintaining the integrity of the borehole 920.

The drill bit 914 may be a coring bit for obtaining core samples from the bottom of the borehole. Alternatively, the bottom-hole assembly may include a sidewall coring tool 926 that can drive a coring bit 929 into the borehole wall to obtain a core sample. The bottom hole assembly may further include one or more logging tools 928 to acquire, e.g., downhole temperature and pressure measurements, as well as a log of effective porosity of the formation. Illustrative porosity logging tools include nuclear magnetic resonance (NMR) logging tools, neutron logging tools, and acoustic logging tools, and combinations thereof. The logging tool measurements may be stored in internal memory for retrieval when the bottom hole assembly returns to the surface, or may be communicated to the surface via mud pulse telemetry or another telemetry technique. A telemetry receiver array 930 may be coupled to tubing below the top drive 910 to receive transmitted telemetry signals. Many telemetry techniques also offer the ability to transfer commands from the surface to the bottomhole assembly, thereby enabling adjustment of the tool's configuration and operating parameters.

Telemetry receiver array 930 is coupled to an interface unit 48, which demodulates and digitizes the telemetry data. A wired or wireless connection 49 enables a computer 50 to receive the measurements of downhole temperature, pressure, and other parameters. Software (represented in FIG. 9 by non-transient information storage media 52) configures the computer 50 to provide a user interface which interact with a user via a keyboard or other input device 54 and a monitor or other output device 56. The user can instruct the computer to retrieve and process the appropriate log parameters and combine them with the laboratory measurements outlined above to determine an initial pressure of a tight gas formation. At various times during the drilling process, the drill string 908 is removed from the borehole to implement a wireline core sampling system such as depicted in FIG. 10.

Figure 10:
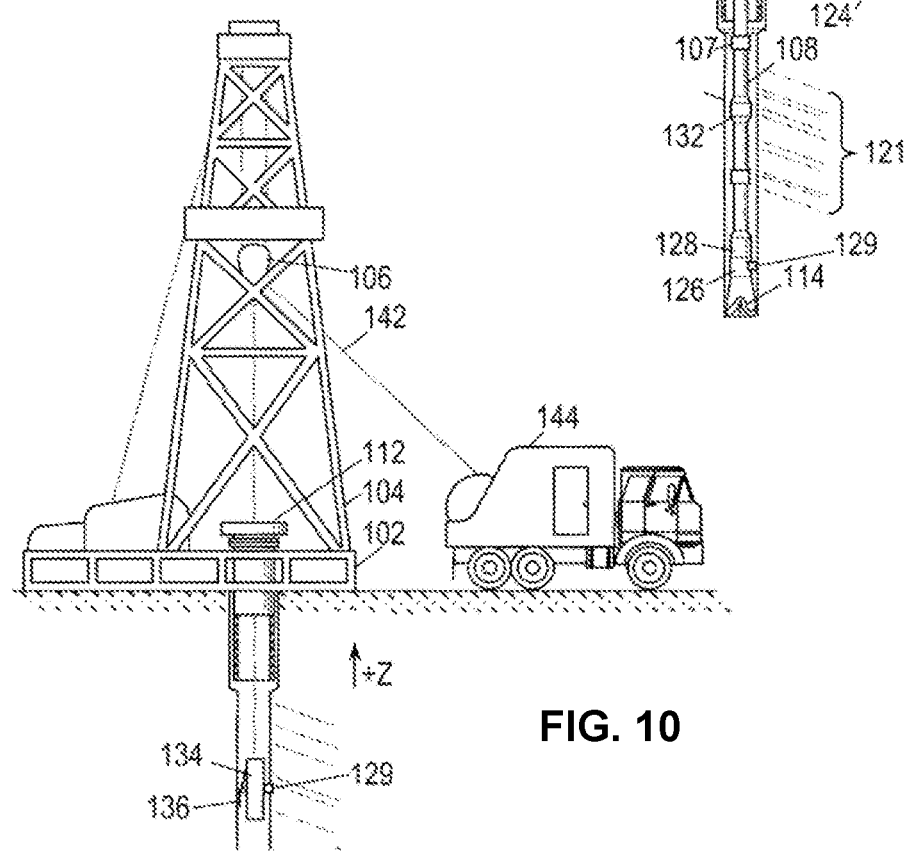
FIG. 10 illustrates an example wireline coring environment, according to some embodiments.

FIG. 10 is an example wireline coring environment, according to some embodiments. Once the drill string has been removed, coring operations can be conducted using a wireline tool assembly 1034 suspended in the borehole by a wireline cable 1042. Wireline cable 1042 has conductors for transporting power to the tool and telemetry from the tool to the surface. The wireline tool assembly 1034 includes one or more logging instruments and a sidewall coring tool with a leveraging arm 1036 that presses the tool against the opposite borehole wall as a coring bit 1029 obtains a core sample. A logging facility 1044 controls the various portions of the tool assembly 1034, collecting measurements from the logging instruments and initiating operation of the coring bit 1029 at one or more selected positions along the borehole. Logging facility 1044 includes computing facilities for processing and storing the measurements gathered by the logging instruments. Such computing facilities can apply the principles outlined herein to determine downhole parameters such as formation pressures and temperatures and borehole pressures and temperatures.

Figure 11:
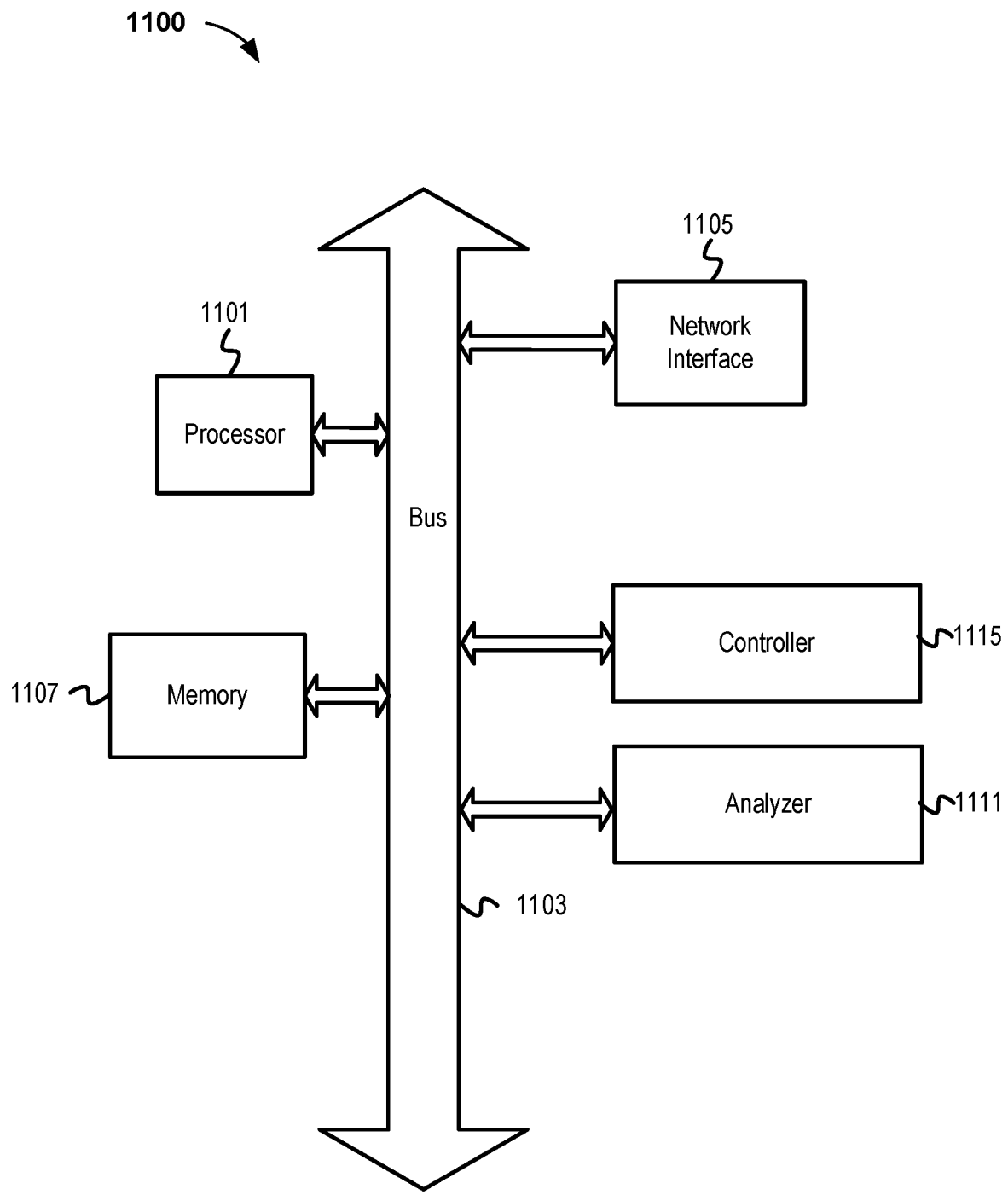
FIG. 11 illustrates an example computer, according to some embodiments.

FIG. 11 depicts an example computer, according to some embodiments. The computer includes a processor 1101 (possibly including multiple processors, multiple cores, multiple nodes, and/or implementing multi-threading, etc.). The computer includes memory 1107. The memory 1107 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 1103 (e.g., PCI, ISA, PCI-Express, HyperTransport® bus, InfiniBand® bus, NuBus, etc.) and a network interface 1105 (e.g., a Fiber Channel interface, an Ethernet interface, an internet small computer system interface, SONET interface, wireless interface, etc.).

The computer also includes an analyzer 1111 and a controller 1115. The analyzer 1011 can perform processing and analyzing of a core sample including determining concentrations of chemical species of gasses such as hydrogen sulfide, carbonates, and other specifies gasses extracted or otherwise release from the core sample. The controller 1115 can control the different operations such as pressure adjustments within a pressurized vessel used to contain the core sample. For example, the controller 1115 can communicate instructions to the appropriate equipment, devices, etc. to alter the pressure within the pressurized vessel based on pressure and temperature measurements as described above. Any one of the previously described functionalities may be partially (or entirely) implemented in hardware and/or on the processor 1101. For example, the functionality may be implemented with an application specific integrated circuit, in logic implemented in the processor 1101, in a co-processor on a peripheral device or card, etc. Further, realizations may include fewer or additional components not illustrated in FIG. 10 (e.g., video cards, audio cards, additional network interfaces, peripheral devices, etc.). The processor 1101 and the network interface 1105 are coupled to the bus 1103. Although illustrated as being coupled to the bus 1103, the memory 1107 may be coupled to the processor 1001.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

While the aspects of the disclosure are described with reference to various implementations and exploitations, it will be understood that these aspects are illustrative and that the scope of the claims is not limited to them. In general, techniques for processing and analyzing of particles from downhole as described herein may be implemented with facilities consistent with any hardware system or hardware systems. Many variations, modifications, additions, and improvements are possible.

EXAMPLE EMBODIMENTS

Embodiment 1: A method comprising: containing a core sample in a containment vessel including dynamically adjusting pressure within the containment vessel to maintain a phase of fluid within the core sample; reducing pressure within the containment vessel; and during or following said reducing pressure, measuring a property of the fluid in the core sample. The method may further comprise desorbing gas from the core sample during said reducing pressure and determining a chemical composition of gas desorbed from the core sample. Said determining a chemical composition of gas desorbed from the core sample may comprise detecting any one of hydrogen sulfide, carbon dioxide, and mercury. Said determining a chemical composition of gas desorbed from the core sample may comprise measuring concentration of a gas component of the desorbed gas at multiple points during desorption of gas from the core sample; and determining an integral amount of the gas component at one or more of the multiple points based on the measured gas component concentrations. The method may further comprise determining a rate of desorption of a gas component of the desorbed gas over a range of phase related fluid property values including at least one of pressure and temperature. Said measuring a property of the fluid in the core sample may comprise determining a saturation point of fluid within the core sample, the saturation point comprising a saturation pressure and a corresponding saturation temperature. The method may further comprise measuring compressibility of the core sample within the containment vessel, and wherein said determining the saturation point including determining the saturation point based, at least in part, on the compressibility of the core sample. The method may further comprise desorbing gas from the core sample during said reducing pressure; and determining a chemical composition of gas desorbed from the core sample. The method may further comprise determining a reservoir production parameter based, at least in part, on the determined chemical composition and the determined saturation point. Said adjusting pressure within the containment vessel may include adjusting pressure within the containment vessel to remain above a saturation point of fluid within the core sample. Said adjusting pressure within the containment vessel may include adjusting pressure within the containment vessel over time based on a detected variation in pressure or temperature of the containment vessel. The method may further comprise, prior to said reducing pressure within the containment vessel, performing a formation material test on the core sample including at least one of a nuclear magnetic resonance test and a computed tomography test. The method may further comprise determining at least one of a porosity and a permeability of the core sample based on the formation material test. The containment vessel may comprise a test containment vessel, and said method may further comprise: extracting, using a coring tool, the core sample from a subsurface formation; depositing the core sample within a transport containment vessel; and applying an initial pressure within the transport containment vessel based, at least in part, on at least one of a measured downhole pressure and a measured downhole temperature.

Embodiment 2: A system comprising: a containment vessel configured to contain a core sample including dynamically adjusting pressure within the containment vessel to maintain a phase of fluid within the core sample; a pressure control system configured to reduce pressure within the containment vessel; and instrumentation configured to measure a property of the fluid in the core sample during or following said reducing pressure. Said pressure control system may comprise a pressure control and gas desorption system configured to desorb gas from the core sample during or following said reducing pressure, and wherein the instrumentation is further configured to determine a chemical composition of gas desorbed from the core sample. Determining a chemical composition of gas desorbed from the core sample may comprise measuring concentration of a gas component of the desorbed gas at multiple points during desorption of gas from the core sample; and determining an integral amount of the gas component at one or more of the multiple points based on the measured gas component concentrations. Measuring a property of the fluid in the core sample may comprise determining a saturation point of fluid within the core sample including determining the saturation point based, at least in part, on the compressibility of the core sample. Said instrumentation may be configured to determine a chemical composition of gas desorbed from the core sample and determine a reservoir production parameter based, at least in part, on the determined chemical composition and the determined saturation point. Said instrumentation may be further configured to determine a rate of desorption of a gas component of the desorbed gas over a range of phase related fluid property values including at least one of pressure and temperature.

The invention claimed is:

1. A method comprising:
   coupling a pressure vessel containing a plurality of core samples with a lab vessel, wherein the plurality of core samples were collected downhole within a borehole and pressure sealed within an interior chamber of the pressure vessel while the pressure vessel remained downhole to maintain a first pressure level in the interior chamber while the pressure vessel is retrieved to a surface area above the borehole and coupled with the lab vessel;
   transferring a number of the plurality of core samples from the pressure vessel to the lab vessel while maintaining the first pressure level in an area surrounding the plurality of core samples, the number of core samples transferred to the lab vessel comprising less than a total number of the plurality of core samples contained in the pressure vessel, including determining the number of the plurality of core samples that are positioned within the lab vessel based on one or more sensor signals provided by an array of sensors extending along and parallel to a longitudinal axis of lab vessel, the one or more sensor signals indicative of a position of one or more pistons or seals within the lab vessel;

isolating the core samples that have been transferred to the lab vessel from the plurality of core samples remaining in the pressure vessel;

controllably reducing a second pressure within the lab vessel in an interior chamber of the lab vessel containing the core samples transferred to the lab vessel and isolated from the plurality of core samples remaining in the pressure vessel while maintaining the first pressure level in the interior chamber of the pressure vessel; and measuring at least one property of one or more fluids contained in the core samples transferred to the lab vessel during or following the controlled reduction of the second pressure within the lab vessel.

2. The method of claim 1, further comprising:

following one or more iterations of transferring a number of core samples to the lab vessel that is less than the total number of the plurality of core samples contained in the pressure vessel, preforming steps comprising:

transferring one or more of the core samples remaining in the pressure vessel to the lab vessel while maintaining the first pressure level in an area surrounding one or more core samples, controllably reducing the second pressure within the lab vessel in the interior chamber of the lab vessel containing the one or more core samples transferred to the lab vessel; and measuring at least one property of one or more fluids contained in the core samples transferred to the lab vessel during or following the controlled reduction of the second pressure within the lab vessel.

3. The method of claim 1, further comprising:

desorbing gas from the core samples that have been transferred to the lab vessel during said reducing pressure; and determining a chemical composition of gas desorbed from the number of core samples.

4. The method of claim 3, wherein said determining a chemical composition of gas desorbed from the core samples that have been transferred to the lab vessel comprises detecting any one of hydrogen sulfide, carbon dioxide, and mercury.

5. The method of claim 3, wherein said determining a chemical composition of gas desorbed from the core samples that have been transferred to the lab vessel comprises:

measuring a concentration of a gas component of the desorbed gas at multiple points during desorption of gas; and determining an integral amount of the gas component at one or more of the multiple points based on the measured gas component concentrations.

6. The method of claim 3, further comprising determining a rate of desorption of a gas component of the desorbed gas over a range of phase related fluid property values including at least one of pressure and temperature.

7. The method of claim 1, wherein said measuring a property of the fluid in the core sample comprises determining a saturation point of fluid within the core samples that have been transferred to the lab vessel, the saturation point comprising a saturation pressure and a corresponding saturation temperature.

8. The method of claim 7, further comprising measuring compressibility of the core samples that have been transferred to the lab vessel, and wherein said determining the saturation point including determining the saturation point based, at least in part, on the compressibility of the core samples that have been transferred to the lab vessel.

9. The method of claim 7, further comprising:

desorbing gas from the core samples that have been transferred to the lab vessel during said reducing pressure; and determining a chemical composition of gas desorbed from the core samples that have been transferred to the lab vessel.

10. The method of claim 9, further comprising determining a reservoir production parameter based, at least in part, on the determined chemical composition and the determined saturation point.

11. The method of claim 1, wherein said maintaining of the first pressure within the pressure vessel includes adjusting pressure within the pressure vessel to remain above a saturation point of fluid within the plurality of core samples contained within the pressure vessel.

12. The method of claim 1, wherein said maintaining of the first pressure within the pressure vessel includes adjusting pressure within the pressure vessel over time based on a detected variation in pressure or temperature of the pressure vessel.

13. The method of claim 1, further comprising, prior to said reducing pressure within the lab vessel, performing a formation material test on the plurality of core samples including at least one of a nuclear magnetic resonance test and a computed tomography test.

14. The method of claim 13, further comprising determining at least one of a porosity and a permeability of the plurality of core samples based on the formation material test.

15. The method of claim 1, further comprising:

extracting, using a coring tool, the plurality of core samples from a subsurface formation;

depositing each of the plurality of core samples with the interior chamber of the pressure vessel; and applying an initial pressure within the interior chamber of the pressure vessel based, at least in part, on at least one of a measured downhole pressure and a measured downhole temperature.

16. A system comprising:

a pressure vessel including a pressure vessel interior chamber, the pressure vessel interior chamber configured to receive and store a plurality of core samples taken from a subsurface formation at one or more downhole locations within a borehole, the pressure vessel configured to maintain a first pressure level within the pressure vessel interior chamber while storing the plurality of core samples in order to maintain a phase of one or more fluids within the plurality of core samples as the pressure vessel is retrieved from within the borehole to a surface area outside of the borehole;

a lab vessel configured to be sealingly coupled to the pressure vessel, the lab vessel including a lab vessel inner chamber configured to receive one or more of the plurality of core samples transferred from the pressure vessel, wherein the lab vessel is configure to maintain the pressurization of the pressure vessel interior chamber as the lab vessel receives a first number of the plurality of core samples that are transferred from the pressure vessel, and to isolate the first number of core samples received at the lab vessel from a second number of the plurality of core samples remaining in the pressure vessel interior chamber, wherein the first number of core samples transferred to the lab vessel is less than a total number of core samples contained in the pressure vessel, the lab vessel further comprising an array of sensors that extends along and in parallel to a length of a longitudinal axis of the lab vessel and configured to detect the position of one or more pistons/seal located within the interior chamber of the lab vessel;

a pressure control system configured to controllably reduce a second pressure within the lab vessel interior chamber containing the first number of the plurality of core samples after the first number of the plurality of core samples have been isolated from the second number of the plurality of core samples and while maintaining the first pressure level within the pressure vessel interior chamber; and instrumentation configured to measure at least one property of the one or more fluids in the first number of the plurality of core samples during or following a controlled reduction of pressure within the lab vessel interior chamber while containing the first number of the plurality of core samples.

17. The system of claim 16, wherein the system, following one or more iterations of transferring the first number of core samples to the lab vessel that is less than the total number of the plurality of core samples contained in the pressure vessel, is further configured to:

transfer one or more of the core samples remaining in the pressure vessel to the lab vessel while maintaining the first pressure level in the area surrounding the one or more core samples;

controllably reduce the second pressure within the lab vessel in the interior chamber of the lab vessel containing the one or more core samples transferred to the lab vessel; and measuring at least one property of one or more fluids contained in the one or more core samples transferred to the lab vessel during or following the controlled reduction of the second pressure within the lab vessel.

18. The system of claim 16, wherein said pressure control system comprises a gas desorption system configured to desorb gas from the first number of the plurality of core samples transferred to the lab vessel during or following said reducing pressure, and wherein the instrumentation is further configured to determine a chemical composition of gas desorbed.

19. The system of claim 18, wherein determining a chemical composition of gas desorbed from the first number of core samples transferred to the lab vessel comprises:

measuring concentration of a gas component of the desorbed gas at multiple points during desorption of gas from the first number of core samples transferred to the lab vessel; and determining an integral amount of the gas component at one or more of the multiple points based on the measured gas component concentrations.

20. The system of claim 18, wherein measuring a property of the fluid in the first number of core samples transferred to the lab vessel comprises determining a saturation point of fluid within the core sample including determining the saturation point based, at least in part, on a compressibility of the number of core samples transferred to the lab vessel.

21. The system of claim 20, wherein said instrumentation is configured to determine a chemical composition of gas desorbed from the first number of core samples transferred to the lab vessel and determine a reservoir production parameter based, at least in part, on the determined chemical composition and the determined saturation point.

22. The system of claim 18, wherein said instrumentation is further configured to determine a rate of desorption of a gas component of the desorbed gas over a range of phase related fluid property values including at least one of pressure and temperature.

* * * * *